(12) United States Patent
Endo et al.

(10) Patent No.: US 7,674,593 B2
(45) Date of Patent: Mar. 9, 2010

(54) PREPARATION METHOD OF BIOTINYLATED PROTEIN AND DETECTION METHOD USING THE SAME

(75) Inventors: Yaeta Endo, Matsuyama (JP); Tatsuya Sawasaki, Matsuyama (JP); Yuko Matsubara, Matsuyama (JP)

(73) Assignee: CellFree Sciences Co., Ltd., Kanagawa (JP)

( * ) Notice: Subject to any disclaimer, the term of this patent is extended or adjusted under 35 U.S.C. 154(b) by 221 days.

(21) Appl. No.: 11/643,737

(22) Filed: Dec. 21, 2006

(65) Prior Publication Data

US 2007/0190579 A1      Aug. 16, 2007

(30) Foreign Application Priority Data

Dec. 28, 2005  (JP)  .............................. 2005-377840
Jun. 30, 2006   (JP)  .............................. 2006-182785

(51) Int. Cl.
*G01N 33/53* (2006.01)
(52) U.S. Cl. ...................... 435/7.1; 435/7.21; 436/501; 436/518; 530/300; 530/350
(58) Field of Classification Search ........................ None
See application file for complete search history.

(56) References Cited

U.S. PATENT DOCUMENTS

| 6,869,774 B2 | 3/2005 | Endo et al. |
| 6,905,843 B1 | 6/2005 | Endo et al. |

FOREIGN PATENT DOCUMENTS

| WO | WO 00/68412 | 11/2000 |
| WO | WO 02/24939 A1 | 3/2002 |
| WO | WO 02/44725 A1 * | 6/2002 |
| WO | WO 2005/035780 A1 | 4/2005 |
| WO | WO 2005/063979 A1 | 7/2005 |

OTHER PUBLICATIONS

Billingsley et al. (Methods in Enzymology, 1990, vol. 184, pp. 451-467).*
Sawasaki et al. (Proceedings of the National Academy of Sciences, USA vol. 99, No. 23, Nov. 12, 2002, pp. 14652-14657).*
U.S. Appl. No. 10/575,807, filed Apr. 13, 2006, Endo et al.
Perkin Elmer Co., Ltd., "A Practical Guide to working with AlphaScreen," from http://las.perkinelmer.com/Content/Manuals/GDE_AlphaScreen_Practical_Guide, Table of Contents (pp. i-iii) and Overview of AlphaScreen (pp. 1-4).
Sawasaki et al., "A cell-free protein synthesis system for high-throughput proteomics," Proc. Natl. Acad. Sci. USA, vol. 99, No. 23, Nov. 12, 2002, pp. 14652-14657.

* cited by examiner

*Primary Examiner*—Lisa V Cook
(74) *Attorney, Agent, or Firm*—Kilyk & Bowersox, P.L.L.C.

(57) ABSTRACT

The present invention presents construction of a detection method requiring no step of removing free biotin during preparation of a biotinylated protein having a biotin tag, in a detection method of a substance interacting with a protein, and studied various preparation methods of the biotinylated protein. In order to solve the above-mentioned problem, the present inventor has found that in a cell-free protein synthesizing system, in particular, a wheat embryo cell-free protein synthesizing system, when biotinylation is performed during or after protein's synthesis, the biotinylation of the protein can be attained in an remarkably lower concentration of the biotin than that in the conventional biotinylation operations, and has accomplished the present invention by using the protein having the biotin tag in each detection system.

11 Claims, 1 Drawing Sheet

PREPARATION METHOD OF BIOTINYLATED PROTEIN AND DETECTION METHOD USING THE SAME

BACKGROUND OF THE INVENTION

1. Field of the Invention

The present invention relates to a preparation method of a biotinylated protein and to a method for detecting a substance interacting with a biotinylated protein, using the protein. More particularly, the invention relates to a detection method wherein a biotinylated protein is prepared in a cell-free protein synthesizing system, and a substance interacting with the protein is detected.

This application claims the priority of Japanese Patent Application Nos. 2006-182785 and 2005-377840, which are incorporated herein by reference.

2. Related Background of the Invention

A variety of methods are utilized for analyzing a biomolecule interaction in an intracellular reaction. Such methods include, for example, ELISA (Enzyme Linked Immunosorbent Assay), DELFIA (Dissociation Enhanced Lanthanide Fluoroimmunoassay), and SPA (Scintillation Proximity Analysis). These methods are referred to as so-called "heterogeneous assay," and used in post-genome researches such as Proteomics, Functional genomics. According to these methods, however, in a detection step, one or more washing operations are required, thus these methods have defects in sample-processing capacity, and the like.

In order to solve the above-mentioned defects, homogeneous (or mix-and-measure) assay technologies have been developed. In the assay technologies, the measurement is performed throughout in a solution state (homogeneous system), and no washing steps are required, but highly accurate data can be obtained. Additionally, since they do not require a solid phase, it is easy to be downsized, which greatly contributes to saving of precious regents, cost reduction, and economy of effort. Typical examples thereof include, for example FRET, BRET, EFC, SPA, FP, and ALPHA.

Of the above-mentioned homogeneous assays, ALPHASCREEN™ commercially available from Perkin-Elmer Corp., which is ALPHA (Amplified Luminescence Proximity Homogeneous Assay), is superior in versatility and quantitativity to other homogeneous assays, because it is not influenced by bonding sites between donor beads and acceptor beads, and uses excitation light with long wavelength, which is little exerted by interference caused by assay components (Non-patent document 1).

On the other hand, in order to efficiently obtain various proteins necessary for the above-mentioned assays, cell-free protein synthetic means are utilized these days. The methods have used rabbit reticulocyte cell-free systems (Reticulocyte Lysate) and *Escherichia coli* extract cell-free systems. However, wheat germ extract preparation methods, and high efficiency cell-free protein synthesis systems using the wheat germ extract, which are based on the clarification of destabilizing mechanism of wheat germ cell-free system (Wheat Germ Extract), and are stable and have high translation activity, are provided (non-patent document 2 and patent documents 1 to 3). Furthermore, screening methods using the wheat germ cell-free protein synthesizing system are provided (patent document 4).

[Non-patent document 1] a home page of PerkinElmer Japan Co., Ltd.
[Non-patent document 2] Proc. Natl. Acad. Sci. USA, 99: 14652-14657 (2002)
[Patent document 1] WO00/68412 A1
[Patent document 2] WO02/24939 A1
[Patent document 3] WO2005/063979 A1
[Patent document 4] WO2005/035780 A1

In various detection methods, biotinylation is performed for labeling proteins (include stabilizing protein). Particularly, in the above-mentioned typical ALPHA product, ALPHASCREEN™ commercially available from PerkinElmer Co., Ltd., in order to analyze interaction between a protein and a biological molecule, a step for biotinylating the protein is essential. In various detection methods, however, presence of a large amount of free biotin derivatives in a reaction solution containing biotin-tagged protein exerts great influences on detection. A step of removing free biotin derivates is necessary, accordingly. Because of this, in various detection methods, particularly in detection steps of ALPHA, the free biotin-removing step before detection makes the operations of whole assay troublesome, and, as a result, they had problems in rapidly analyzing polyspecimen.

SUMMARY OF THE INVENTION

As a method for solving the above-mentioned problems, the present inventor has found that when in a cell-free protein synthesizing system, the protein is biotinylated during or after the protein's synthesis, the biotinylation of the protein can be attained in a more remarkably lower concentration of biotin derivative than that used in conventional biotinylation operations, and has accomplished the present invention by using the biotin-tagged protein in each detecting system without removing free biotin derivative, in particular ALPHASCREEN™.

That is, the present invention comprises the following aspects:

1. a biotinylated protein which is obtained by synthesizing a protein in the presence of a biotinylating enzyme and a biotin derivative;
2. a method for detecting a substance interacting with a protein, wherein a biotinylating enzyme and a biotin derivative are activated with a protein containing a biotin tag during or after the protein's synthesis to prepare a biotinylated protein, subsequently a substance interacting with the biotinylated protein is detected;
3. the detection method of previous aspect 2, wherein after the preparation of the biotinylated protein, the substance interacting with the biotinylated protein is detected without removing the biotin derivative which did not bond to the protein containing a biotin tag;
4. the detection method of previous aspect 2, which is at least one selected from 1) ALPHA, 2) surface plasmon resonance technique, 3) fluorescence correlation spectroscopy, 4) fluorescence intensity distribution analysis, 5) ELISA, 6) DELFIA, 7) SPA, 8) FRET, 9) BRET, 10) EFC, and 11) FP;
5. . the detection method of previous aspect 3, which is at least one selected from 1) ALPHA, 2) surface plasmon resonance technique, 3) fluorescence correlation spectroscopy, 4) fluorescence intensity distribution analysis, 5) ELISA, 6) DELFIA, 7) SPA, 8) FRET, 9) BRET, 10) EFC, and 11) FP;
6. the detection method of previous aspect 2, wherein the biotinylated protein is fixed to a carrier through a biotin linkage to detect the substance interacting with the biotinylated protein;
7. the detection method of previous aspect 3, wherein the biotinylated protein is fixed to a carrier through a biotin linkage to detect the substance interacting with the biotinylated protein;

8. the detection method of previous aspect 4, wherein the biotinylated protein is fixed to a carrier through a biotin linkage to detect the substance interacting with the biotinylated protein;
9. the detection method of previous aspect 2, wherein the substance interacting with the biotinylated protein is detected using a labeled substance of the biotin derivative as a marker;
10. the detection method of previous aspect 3, wherein the substance interacting with the biotinylated protein is detected using a labeled substance of the biotin derivative as a marker;
11. the detection method of previous aspect 4, wherein the substance interacting with the biotinylated protein is detected using a labeled substance of the biotin derivative as a marker;
12. the detection method of previous aspect 6, wherein the substance interacting with the biotinylated protein is detected using a labeled substance of the biotin derivative as a marker;
13. a method for detecting a biomolecule interaction using Amplified Luminescence Proximity Homogeneous Assay, comprising the steps of:
   1) preparing a protein containing a biotin tag in a cell-free protein synthetic means,
   2) activating the protein containing the biotin tag with a biotinylating enzyme and a biotin derivative to prepare a biotinylated protein,
   3) bonding directly or indirectly a biological molecule which possibly interacts with a protein to acceptor beads, and
   4) contacting the biotinylated protein prepared in the step 2), the acceptor beads prepared in the step 3), and donor beads to which streptavidin is bonded to cause a signal change due to the proximity of the acceptor beads and the donor beads, thereby to detect an interaction of the protein with the biological molecule;
14. the method of previous aspect 13, wherein the step 1) and the step 2) are performed at the same time; and
15. a method for screening an autophosphorylated protein using Amplified Luminescence Proximity Homogeneous Assay, comprising the steps of:
   1) preparing a candidate autophosphorylated protein containing a biotin tag in a cell-free protein synthetic means,
   2) activating the candidate autophosphorylated protein containing the biotin tag with a biotinylating enzyme and a biotin derivative to prepare a biotinylated candidate autophosphorylated protein,
   3) bonding a phosphorylated detection antibody directly or indirectly to acceptor beads, and
   4) contacting the biotinylated candidate autophosphorylated protein prepared in the step 2), the acceptor beads prepared in the step 3), and donor beads to which streptavidin is bonded to cause a signal change due to the proximity of the acceptor beads and the donor beads, thereby to detect a phosphorylation activity.

EFFECTS OF THE INVENTION

The method for preparing a biotinylated protein according to the present invention enables a rapid analysis of polyspecimen, because it does not require a step of removing free biotin derivatives.

DESCRIPTION OF THE PREFERRED EMBODIMENTS

Figure 1:
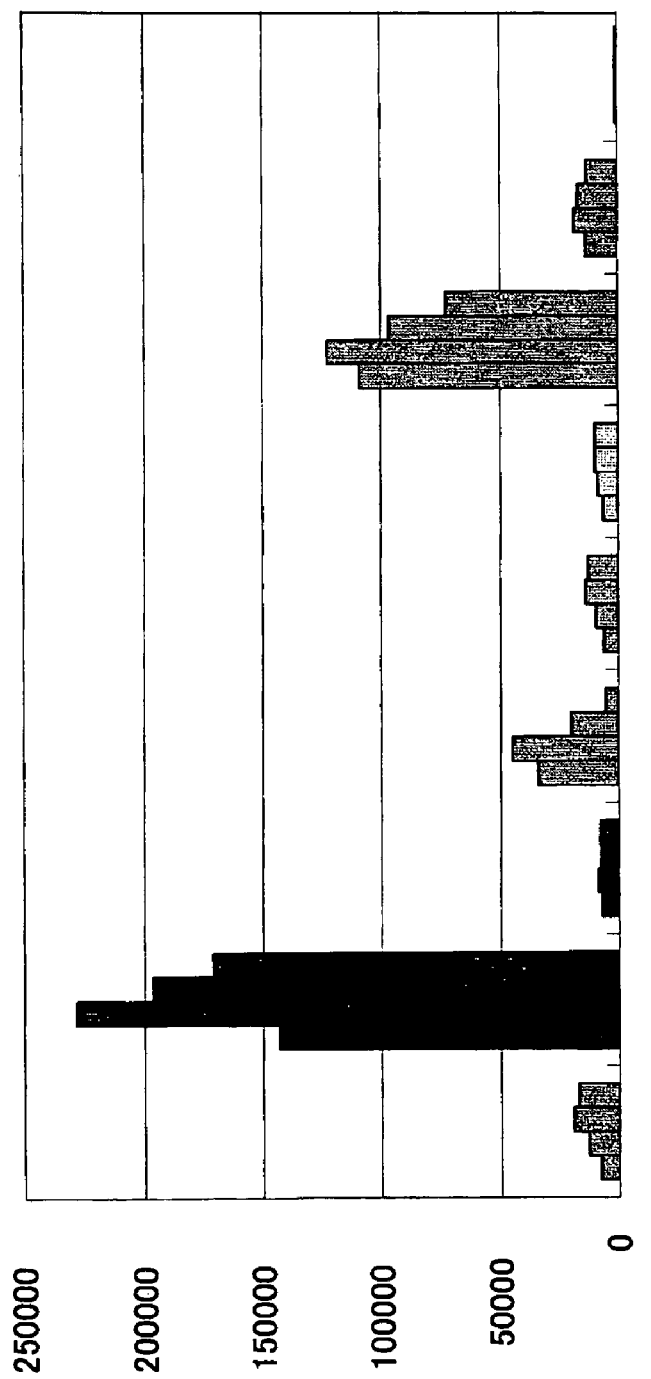
FIG. 1 shows detection results of an autophosphorylated protein wherein lanes show amounts of each protein (0.5, 1.0, 2.0, 3.0 µl/25 µl) from the left lane.

Hereinafter, the terms used herein will be defined.

Protein Containing a Biotin Tag

The term "protein containing a biotin tag" refers to a fused protein of a protein bearing a binding tag sequence for biotin. Preferable examples of the protein include autophosphorylated proteins. In addition, the proteins, for example, also include candidate protein kinase which are expressed by selecting a potential sequence of protein kinase gene from a full length cDNA of mouse which is a mammal model.

Biotin Derivative

The term "biotin derivative" refers to a compound capable of bonding to biotin, norbiotin, homobiotin, oxybiotin, iminobiotin, desthiobiotin, diaminobiotin, biotin sulfoxide, biotin sulfone, avidin or streptavidin and combination thereof.

The biotin derivatives also include the above-mentioned biotin derivatives with a labeling substance such as GFP, BFP, CFP, RFP, YFP, EGFP, ECFP, ERFP, EYFP or TMR, or fluorescence substance such as CY3, CY5, TAMRA, Fluorescein, ROX, HEX, TET, BODIPY® (Invitrogen Japan K.K). In addition, the biotin derivatives include the above-mentioned biotin derivative with a puromycin derivative (Pur) as a labeling substance.

In addition, the above-mentioned biotin derivatives include biotin derivative with radio isotope or stable isotope (heavy hydrogen, $C^{13}$, $N^{15}$ or like).

When the biotinylation of the protein containing a biotin tag is performed by using the biotin derivative with the labeling substance, a biotinylated protein with the labeling substance can be obtained. Accordingly, when the labeling substrate is used as a marker, a substance interacting with a protein can be detected, without fixing the protein to a carrier through a biotin linkage.

Herein, the carrier used in the present invention is not particularly limited as long as it can fix the protein through a biotin linkage, and inactive carriers such as resin, for example microplates used in usual biochemical experiments, can be used as the carrier.

Biotinylated Protein

The term "biotinylated protein" refers to a protein which is biotinylated by activity of a biotinylating enzyme in the presence of a biotin derivative.

Substance Interacting with a Protein

A substance interacting with a protein is not limited to biological molecules as long as it interacts with the protein, but biological molecules are preferable. Examples of interacting substance for the protein include: an antibody for an antigen; an antigen for an antibody; a hormone (such as insulin) for a hormone receptor (such as an insulin receptor); a hormone receptor (such as an insulin receptor) for a hormone (such as insulin); and a corresponding sugar chain for a lectin. The biological molecules also include fragments and subunits thereof having specific bonding ability. Further, these biological molecules bond directly or indirectly to acceptor beads. The molecules bonding directly to the acceptor beads can be obtained by utilizing bonding methods known per se. When the biological molecule is very expensive or is difficult to obtain, in order to minimize the amount of the biological molecule used, the molecule can be indirectly bonded to the protein, utilizing an antibody or protein A recognizing the biological molecule. In a case of an autophosphorylated protein as a protein, for example, an antibody detecting phosphorylation is used as the biological molecule.

A step of removing the biotin derivative which did not bond to the protein

Usually, the biotinylation is performed by using the biotin derivative in an excessive amount over the equivalent to the protein to be bonded. After the biotinylation, the biotin derivative which did not bond to the protein is removed through a G-25 spin column. According to method of preparing the biotinylated protein of the present invention, however, the biotinylation can be sufficiently performed in a lower amount of the biotin derivative compared with the usual biotinylation, and thus the step of removing the biotin derivative which did not bond to the protein is not necessary.

Interaction

The term "interaction" means that the protein bonds to the biological molecule through, but not limited to, covalent bonding, hydrophobic bonding, hydrogen bonding, van der Waals bonding, electrostatic force, or the like. In particular, examples of the substance causing the interaction include agonists, antagonist, inverse agonists, inhibitors, promoters against the action of the biological molecule. Further, synthesis reactions and decomposition reactions of the newly produced substances caused by the above-mentioned action are included in the interaction.

Specifically, 1) bonding action of a protein with a protein, 2) kinase activity, 3) protease activity and the like, in use of ALPHA, will be exemplified below. The interaction is not limited to the examples mentioned below, and various detection systems can be utilized.

1) Bonding Action of a Protein with a Protein

The protein is biotinylated, and the protein as the biological molecule is bonded to acceptor beads. If there is bonding action between the protein and the biological molecule, increased signal can be detected by proximity of the donor beads and the acceptor beads.

2) Kinase Activity

The protein is biotinylated, and the corresponding biological molecule, the phosphorylated detecting antibody is bonded to acceptor beads. The protein is autophosphorylated by adding kination Buffer. If the protein can be autophosphorylated and bonded to the phosphorylated detecting antibody, increased signal can be detected by proximity of the donor beads and the acceptor beads.

3) Protease Assay

The protein is biotinylated, and the corresponding antibody recognizing the protein is bonded to acceptor beads, whereby increased signal can be detected by proximity of the donor beads and the acceptor beads. Subsequently, the addition of protease causes cleavage of the protein due to the protease action, thereby decreased signal can be detected by separation of the donor beads and the acceptor beads.

FRET (Fluorescence Resonance Energy Transfer)

FRET is a procedure utilizing the energy transfer between two kinds of fluorescence substances referred to as donor and accepter. Typical examples thereof include ALPHA mentioned below.

ALPHA (Amplified Luminescence Proximity Homogeneous Assay)

As ALPHA, ALPHASCREEN™ (PerkinElmer Co., Ltd.) is a typical assay.

The analysis method is based on the movement of singlet oxygen between donor beads and acceptor beads which are proximate to each other. In an excitation at 680 nm, a photosensitizer in the donor beads converts ambient oxygen into singlet oxygen, and the singlet oxygen spreads to 200 nm. Chemiluminescent groups in the acceptor beads move energy to the fluorescent acceptor in the beads, and subsequently emit light at about 600 nm.

That is, the biotin of the biotinylated protein is bonded to the streptavidin of the donor beads. When the two kinds of the beads come close to each other due to the interaction between the biotinylated protein and the biological molecule, the cascade of the chemical reaction starts, and greatly amplified signal is generated. The typical biomolecule interaction detection method based on this principle is ALPHA.

Acceptor Beads

They are inactive carriers such as glass, silica gel, and resins, and are used for fixing the above-mentioned biological molecule.

Donor Beads

They are inactive carriers such as glass, silica gel, and resins, and are used for fixing streptavidin.

Surface Plasmon Resonance Method (SPR)

The biotinylated protein obtained in the method for preparing a biotinylated protein according to the present invention is fixed to a metal film through a biotin linkage. Then, a solution containing each biological molecule is poured into the SPR to detect a substance interacting with the protein using, as a marker, change of the photorefractive index between the biotinylated protein fixed on the metal film and the biological molecule. The measurement in this case can be performed using usual surface plasmon resonance methods.

Fluorescence Correlation Spectroscopy (FCS)

A synthetic liquid (preferably, obtained after synthesis of a cell-free protein) containing the biotinylated protein obtained in the method for preparing a biotinylated protein according to the present invention is diluted with a suitable diluent and contacted with each biological molecule, subsequently subjected to detection on a measuring device in situ. Since the measurement is performed by irradiating laser beam to measure the fluctuation of fluorescent molecule (labeling substance of biotin derivative) in the liquid, the pH and measuring time are not particularly limited, and the measurement can be performed at room temperature. In the FCS measurement, the fluctuation of fluorescent molecule within a micro area is measured, and a translation diffusion time is found based on the obtained information. Using the translation diffusion time as a marker, a substance interacting with the protein is detected.

Besides, FCS includes FCCS (Fluorescence cross-correlation spectroscopy) which is ameliorative measures of FCS.

Fluorescence Intensity Distribution Analysis (FIDA)

A synthetic liquid (preferably, obtained after synthesis of a cell-free protein) containing the biotinylated protein obtained in the method for preparing a biotinylated protein according to the present invention is diluted with a suitable diluent and contacted with each biological molecule, subsequently subjected to detection on a measuring device in situ. Since the measurement is performed by irradiating laser beam to measure the fluctuation of fluorescent molecule (labeling substance of biotin derivative) in the liquid, the pH and measuring time are not particularly limited, and the measurement can be performed at room temperature. In the FIDA measurement, fluorescence intensity and the number of the fluorescent molecules within a micro area are measured. Using the measured fluorescence intensity and the number as markers, a substance interacting with the protein is detected.

Fluorescence Polarization (FP)

A synthesis liquid containing the biotinylated protein obtained by the method of preparing the biotinylated protein of the present invention (preferably a synthesis liquid after a cell-free protein synthesis) is diluted with a suitable diluent and is contacted with each biological molecule, which is directly detected on a measurement device. The fluorescence polarization is a measurement method based on the property that the fluorescence emitted from a fluorescence substance, by irradiating polarized excitation light to the fluorescence substance, shows different polarization depending on the molecular weight. When the fluorescence labeled substance (labeled substance of the biotin derivative) is bonded to a high molecular weight compound such as an antibody or a receptor, the apparent molecular weight becomes higher, thereby the molecular movement becomes smaller, resulting in the emission of the fluorescence maintaining the polarization (high degree of polarization). Using the fluorescence maintaining the polarization as a marker, a substance interacting with a protein is detected.

ELISA (Enzyme-Linked Immuno Adsorbent Assay)

The biotinylated protein obtained by the method of preparing the biotinylated protein of the present invention is fixed to a plate through biotin linkage. Next, each biological molecule and then a labeled antibody specifically recognizing the biological molecule are added to the plate. When the biotinylated protein is interacted with, particularly bonded to each biological molecule, the labeled antibody is not removed from the plate by washing. Using the label of the labeled antibody as a marker, a substance interacting with a protein is detected.

DELFIA (Dissociation Enhanced Lanthanide Fluoro immuno Assay)

DELFIA is utilized in solid phase analysis, in which the antibody is usually labeled with europium or other lanthanides, and the antibody without the europium label is removed by washing, and then the europium fluorescence is detected. Using the fluorescent marker, a substance interacting with a protein is detected.

SPA (Scintillation Proximity Analysis)

SPA utilizes biotin/avidin interaction to capture a radiolabeled substrate. The biotinylated protein obtained by the method of preparing the biotinylated protein of the present invention is captured by streptavidin. In SPA detection, the streptavidin is bonded to beads containing a scintillant, whereas in flush plate detection, the streptavidin is bonded to the inside of wells in a microplate containing a scintillant. After fixation, the radiolabeled substrate approaches the scintillant at a distance enough to stimulate the emission of light. Using the light change caused by the proximity as a marker, a substance interacting with a protein is detected.

EFC (Enzyme Fragment Complementation)

EFC analysis is based on a processed β-galactosidase comprising two fragments, namely an enzyme acceptor (EA) and an enzyme donor (ED). When the fragments are separated, the β-galactosidase activity is lost, whereas when the fragments are combined, they are linked (complementarily) to form an active enzyme. EFC analysis utilizes the ED-analyte combination. In this case, the analyte can be recognized by a specifically bonded protein such as an antibody or a receptor. In the absence of the specifically bonded protein, the ED-analyte combination complements EA, can form an active β-galactosidase, and generates a positive luminescent signal. When the ED-analyte combination is bonded to the specifically bonded protein, the complement with EA is inhibited, and the signal is not generated. When free analyte is supplied (in a sample), the analyte compete against the ED-analyte combination with respect to the bonding to the specifically bonded protein. The free analyte releases the ED-analyte combination for complement with EA, and signal is generated depending on the amount of the free analyte in the sample.

BRET (Bioluminescent Resonance Energy Transfer)

It is an assay utilizing bioluminescent resonance energy transfer, wherein energy is transferred to a fluorescent protein through bioluminescent-generating reaction of luciferase.

The biotinylated protein obtained in the method for preparation a biotinylated protein according to the present invention can be utilized in the above-mentioned measuring systems without a step for removing free biotin derivatives.

Preparation Method of a Biotinylating Enzyme

In one aspect of the present invention, a biotinylating enzyme is prepared in a cell-free protein synthesizing system, particularly in a wheat embryo cell-free protein synthesizing system. Specifically, a gene sequence coding a biotinylating enzyme of *E. coli* genom is produced with a vector, and prepared in a wheat embryo cell-free protein synthesizing system. However, commercially available biotinylating enzymes (such as Biotin-Protein Ligase-BIRA 500 Kit available from AVIDITY, LLC) can also be used.

Preparation Method of a Biotinylated Protein

In one aspect of the present invention, during a preparation of a protein containing a biotin tag in a cell-free protein synthesizing system, particularly in a wheat embryo cell-free protein synthesis, translation reaction is performed in the presence of a feed solution containing a suitable amount of a biotinylating enzyme and a biotin derivative. In other words, the step of synthesizing the protein and the biotinylation step are simultaneously performed. This principle is applicable to various methods, and the biotinylating enzyme, biotin derivative is present at an optimum concentration in an upper layer, a feed phase and in a lower layer, a reaction phase according to a double layer method; in a feed solution according to a dialysis; and in a replenisher, a feed solution, according to a batch method.

In another aspect of the present invention, after the protein containing a biotin tag is prepared, the biotinylating enzyme and the biotin derivative can be added thereto to perform the biotinylation.

The optimum final concentration of the biotin derivative in the translation reaction which is the preparation stage of the protein is from about 0.1 to about 1.0 μM, preferably from about 0.3 to about 0.7 μM. In a usual biotinylation, the biotin concentration is from about 30 to about 70 μM. The optimum final concentration of the biotinylating enzyme in the translation reaction is from about 0.8 to about 1.5 μM.

In case where the present invention is applied to the double layer method, the biotin derivative is kept in the upper layer, the feed phase. In the lower layer, the reaction phase, the biotin derivative and the biotinylating enzyme are kept.

In case where the present invention is applied to the dialysis, the biotin derivative and the biotinylating enzyme are kept on the feed solution side. It is of course preferable that the biotin derivative and the biotinylating enzyme are kept on the reaction liquid side, the reaction phase, but it is enough for biotinylation of the protein to keep the biotin derivative and the biotinylating enzyme on the reaction liquid side and the biotin derivative on the feed liquid side.

In case where the present invention is applied to the batch method, it is preferable that the biotin derivative and the biotinylating enzyme are kept on the replenisher side. In the batch method, it is impossible to add the biotin derivative and the biotinylating enzyme during the reaction, and thus it is also preferable to previously keep optimum concentration of the biotin derivative and the biotinylating enzyme in the reaction solution.

mRNA used in the translation reaction of the system of the present invention is preferably prepared by amplifying and synthesizing a biotin-tagged gene and a target gene in PCR method to obtain a DNA template and by subjecting it to transcription reaction without introduction to a plasmid, but, mRNA amplified by introducing to a plasmid can be of course used. In addition, as mentioned below, with respect to the transcriptional product obtained by transcription reaction, the crude transcription solution, which is not subjected to alcohol precipitation and the like, can be directly introduced into the translation reaction system. The translation template purified by means of alcohol precipitation can also be introduced into the translation reaction system.

Hereinafter, general steps of the cell-free protein synthetic means utilized in the preparation of a biotinylated protein according to the present invention will be described.

(1) Step of Preparing a Transcription Template

The term "transcription template" refers to DNA which can be used as a template molecule in in vitro transcription reaction, which has at least a biotin tag and a base sequence coding a target protein, a target protein downstream of a suitable promoter sequence. The suitable promoter sequence refers to a promoter sequence which can be recognized by an RNA polymerase used in a transcription reaction, and examples thereof include, for example, SP6 promoter, T7 promoter. Any DNA coding a target protein may be used.

It is preferable that the transcription template has a base sequence with activity to control the translation efficiency between the promoter sequence and the base sequence coding the biotin tag and the protein. For example, 5'-untranslated region derived from RNA virus like Ω sequence from tobacco mosaic virus and/or Kozak's sequence may be used. In addition, preferably, the transcription template has 3'-untranslated region containing a transcription termination region and the like downstream of the base sequence coding the biotin tag and the target protein. As the 3'-untranslated region, about 1.0 to about 3.0 kbp regions downstream of the termination codon is preferably used. These 3'-untranslated regions are not necessarily original genes per se coding the target protein.

In the transcription, the crude reaction product without any purification, which is obtained by the amplification and the synthesis of the DNA coding the biotin tag and the target protein in PCR method, can be used as the transcription template. The transcription template DNA thus obtained can be purified by chloroform extraction or alcohol precipitation, and the purified DNA may be subjected to the transcription reaction. According to the protein's synthesis of the present invention, however, the reaction solution after PCR reaction can be used in situ as the transcription template solution. Since the template DNA is not introduced into an expression plasmid in the preparation of the transcription template, an *E. coli* transformation step and a step of selecting clone into which the template DNA is introduced are not necessary. Further, this method can remarkably omit the steps and can synthesize a large amount of the transcription template in a small number of steps for a short period of time, compared with a method in which a large amount of plasmid is once prepared and treated with restriction enzyme to give a transcription template. That is, since the preparation step of the plasmid in which the DNA coding the target protein is introduced is not necessary, a time to ultracentrifuge for purification of the plasmid can be shortened. Also, because the restriction enzyme treatment for cutting the transcription template off from the plasmid, the phenol treatment or the chloroform treatment for removing the restriction enzyme and the like, the alcohol precipitation for purifying the transcription template, a step for dissolving the DNA precipitation, the transcription template can be omitted, inhibition of the transcription reaction caused by the remaining phenol/chloroform, and the loss of the transcription template due to the multi-step of purification operation is improved. In addition, in a series of the protein synthesis steps, (1) a step of precipitating a translation template in the reaction liquid after the transcription reaction, (2) a step of removing a supernatant liquid in the reaction liquid after the transcription reaction, and (3) a centrifugation procedure necessary in a drying step after the removing step (2) are not necessary. Furthermore, since the number of the steps necessary for the reaction can be reduced, the number of chips used can be advantageously reduced.

(2) Transcription Reaction Step

A translation template mRNA is prepared by in vitro transcription reaction, from the transcription template DNA coding the biotin tag and the target protein (including the DNA introduced into the expression plasmid), which are prepared in the known method per se; or the transcription template DNA coding the biotin tag and the target protein which are prepared using the crude DNA amplified and synthesized in the PCR method mentioned in the item (1). In this step, a solution containing the transcription template, preferably a PCR reaction liquid, which is provided in a reaction system (for example, a commercially available container such as 96-well titer plate), and a solution containing components necessary for the transcription reaction such as RNA polymerase compatible with the promoter in the transcription template (for examples, SP6 RNA polymerase and the like) or a substrate for RNA synthesis (4 kinds of ribonucleoside triphosphates) (also referred to as a "solution for a transcription reaction") are mixed, and the mixture was incubated at about 20 to about 60° C., preferably about 30 to about 42° C. for about 30 minutes to about 16 hours, preferably about 2 to about 5 hours.

The mRNA to be a translation template can be transcribed with SP6 RNA polymerase (supplied by Promega Corporation), using a circle plasmid DNA in which an Ω sequence part is replaced by a base sequence of SEQ ID NO. 136 described in WO03/056009 as a template, for example, on the basis of PEU-GFP vector (Sawasaki, T. et al., PNAS, 99 (23), 14652-7 (2002)) to which GFP gene DNA (Chiu, W. – L.,et al., Curr. Biol.6, 325-330 (1996)) is inserted.

The reaction liquid obtained after the conventional transcription reaction has unreacted ribonucleoside triphosphate, a by-product, pyrophoric acid, and salts which are included in the solution for transcription reaction, in addition to the translation template RNA, and thus it was necessary to selectively precipitate the translation template to separate and remove the unreacted substrates, because it was known that these substances inhibit the subsequent translation reaction. Accordingly, the translation template in the reaction liquid obtained in the transcription reaction was precipitated, and a supernatant containing unreacted ribonucleoside triphosphate, a by-product, pyrophoric acid, and salts which are included in the solution for transcription reaction was removed, and further the precipitation was dried until components capable of inhibiting the translation reaction in the remaining supernatant (such as alcohol) could be removed. However, in the transcription reaction for synthesizing mRNA used in the protein synthesis of the present invention, even if (1) the step of precipitating the translation template in the reaction liquid after transcription, (2) the step of removing the supernatant in the reaction liquid after transcription, and (3) the step of drying the resulting product after the removing in step (2) (the steps (1) to (3) being also referred to as "purification step for mRNA") are omitted, the translation efficiency is not lowered. That is, the crude mRNA in the present invention means a transcription solution containing mRNA after transcription reaction without any purification operation.

According to the method of the present invention, any of 1) the crude mRNA prepared by amplifying and synthesizing the target gene with the PCR method to obtain the DNA template, and performing the transcription reaction without introduction into a plasmid (referred also to as "PCR-based crude mRNA"), 2) mRNA prepared by amplifying and synthesizing the target gene with the PCR method to obtain the DNA template, and by purifying the translation template prepared by transcription reaction without introduction into a plasmid using ethanol precipitation (referred to as "purified mRNA" in order to distinguish the crude mRNA, and referred also to as "PCR-based purified mRNA"), 3) the crude mRNA prepared by introduction into the plasmid and transcription reaction (referred also to as "plasmid-based crude mRNA"), 4) the purified mRNA prepared by introduction into the plasmid and transcription reaction (referred also to as "plasmid-based purified mRNA) can be added to a protein synthesis cell extract for the translation.

Also, as the cell extract for protein synthesis used herein, any extracts that can translate the translation template and produce a protein coded by the template may be used and examples thereof include cell extracts of E. coli, embryos of plant seeds, rabbit reticulocyte and cultured insect cells used in baculovirus expression system. Commercially available products can be used as such an extract, and the extract can be prepared by known method per se, specifically by a method described in Pratt, J. M. et al., Transcription and Translation, Hames, 179-209, B. D. &Higgins, S. J., eds), IRL Press, Oxford (1984) and the like in the case of the E. coli extract.

In addition, protein synthesis system using living cell of E. coli, CHO or baculovirus expression system may be used in the present invention.

Examples of the commercially available cell extract for protein synthesis include an attachment in E.coli S30 extract system (supplied by Promega Corporation), an attachment in RTS 500Rapid Translation System (supplied by Roche Inc.) in the case of extracts from E. coli; an attachment in Rabbit ReticulocyteLysate Sytem (supplied by Promega Corporation) in the case of extracts from rabbit reticulocyte; and an attachment in PROTEJOS™ (supplied by TOYOBO CO., LTD.) in the case of extracts from wheat embryo. Above all, it is preferable to use the extract system of embryos of plant seeds. Preferable examples of the plant seed include seeds of graminaceous species such as wheat, barley, rice and corn, seed of spinach, and wheat seed embryo extract is particularly preferable. Wheat seed embryo extracts from which an endosperm component and "low-molecular-weight substances inhibiting the protein synthesis" during the preparation step of the extract are substantially removed are more preferable, because they have more decreased components and substances inhibiting the protein synthesis in the extract than the conventional wheat seed embryo extracts.

The best cell extracts applicable to the present invention are extracts from wheat embryo, and the extracts from which the endosperm component and metabolite such as glucose, which inhibit the protein synthesis in the embryo tissue cell, are substantially removed. For more information, endosperm component contaminated in embryo extract is substantially removed from the embryo extract. The term "cell extract wherein endosperm component is substantially removed from the cell extract" means that a cell extract having not more than 7%, preferably not more than 1% of a ribosome adeadenylation rate. More preferably, the cell extract substantially has sugar and phosphorylated sugar reduced to not more than 10 mM, preferably not more than 6 mM (as a glucose concentration in the extract having an absorbance of 200 OD/ml at 260 nm).

In addition, a preparation method of thus cell extract is exemplified in WO 2005/063979 A1 gazette.

(3) Translation Reaction Step

To the thus obtained, cell extract for protein synthesis to which the purified mRNA or the crude mRNA is added, a solution containing components necessary or suitable for translation reaction (referred also to as "solution for translation reaction") such as 3',5'-cAMP, an amino acid as a substrate, energy source, various ions, buffer, an ATP regenerating system, a nucleolytic enzyme inhibitor, a tRNA, a reducing agent, polyethylene glycol, folate, and antibacterial agent is added, which is incubated at a temperature suitable for the translation reaction for a adequate time to perform the translation reaction. The amino acids as substrates are generally 20 kinds of natural amino acids constructing a protein, and analogs or isomers thereof may be used for the purpose. Examples of the energy source include ATP and/or GTP. Various ions include ions of acetates such as potassium acetate, magnesium acetate, ammonium acetate and glutamates. As the buffer, Hepes-KOH, Tris-acetate and the like may be used. Examples of the ATP regenerating system include a combination of phosphoenolpyruvate and pyruvate kinase, a combination of creatine phosphate and creatine kinase. Examples of the nucleolytic enzyme inhibitor include RNase inhibitor, nuclease inhibitor. Herein, as example of the RNase inhibitor, RNase inhibitor from human placenta (supplied by TOYOBO CO., LTD. and the like) and the like are used. The tRNA may be obtained by the method described in Moniter, R., et al., Biochim. Biophys. Acta.,43, 1 (1960) and the like, alternatively, commercially-available products can be used. The reducing agent includes dithiothreitol and the like. The antibacterial agent includes sodium azide, ampicillin and the like. The additive amounts thereof are, as required, selected within the range that they are usually used in the cell-free protein synthesis.

The addition mode of the translation reaction solution may be, as required, selected depending oh the translation reaction system to be used. As the translation reaction system used in the method of the present invention, any systems applicable to the cell-free protein synthesis method of the present invention, such as a batch method (Pratt, J. M. et al., Transcription and Translation, Hames, 179-209, B. D. &Higgins, S. J., eds, IRL Press, Oxford(1984)); a continuous cell-free protein synthesis in which 3',5'-cAMP, an amino acid, energy source and the like are continuously supplied to the reaction system (Spirin,A. S. et al., Science, 242, 1162-1164(1988)); a dialysis (Kigawa et al. ,21th The Molecular Biology Society of Japan, WID6); or a double layer method (WO02/24939) and the like may be used. Furthermore, a discontinuous gel filtration wherein a template RNA, 3',5'-cAMP, an amino acid, energy source and the like are, supplied to the synthesis reaction system when necessary, and synthetic products and decomposed products are exhausted when necessary (Japanese Patent Application Laid-open No. 2000-333673); a method wherein a synthesis reaction tank is prepared by a carrier capable of molecular-sieving, the above-mentioned materials for synthesis and the like are developed using the carrier as a mobile phase, the synthesis reaction is carried out during the development, and the resulting protein can be recovered (Japanese patent Application Laid-open No. 2000-316595) can also be used. However, the batch method and the double layer method are preferable from the viewpoint of the simplification of the synthesis system structure, space saving, low cost, and provision of a polyspecimen simultaneous synthesis system applicable to a high throughput analysis, and the double layer method are particularly preferable from the viewpoint that a relatively large amount of protein can be obtained.

When the translation reaction is performed in the batch method, the translation reaction solution containing biotin derivative and the biotinylating enzyme may be added to the cell extract for protein synthesis to which the crude mRNA or the purified mRNA is added to mix them. Alternatively, when the components contained in the translation reaction solution containing the biotin derivative and the biotinylating enzyme are previously mixed with the cell extract for protein synthesis, the addition of the translation reaction solution can be omitted. As the "translation reaction liquid" which is obtained by mixing the cell extract for protein synthesis to which the crude mRNA or the purified mRNA is added, with the translation reaction solution containing the biotin derivative and the biotinylating enzyme, when using, for example, a solution containing 0.1 to 1.0 µM of a biotin derivative, 0.8 to 1.5 µM of a biotinylating enzyme, 1 to 3 mM of cAMP, 10 to 50 mM of HEPES-KOH (pH 7.8), 55 to 120 mM of potassium acetate, 1 to 5 mM of magnesium acetate, 0.1 to 0.6 mM of spermidine, respectively 0.025 to 1 mM of L-amino acids, 20 to 70 µM, preferably 30 to 50 µM of DTT, 1 to 1.5 mM of ATP, 0.2 to 0.5 mM of GTP, 10 to 20 mM of creatine-phosphate, 0.5 to 1.0 units/µl of an RNase inhibitor, 0.01 to 10 µM of a protein disulphide isomerase and 24 to 75% wheat embryo extract and the like may be used. When such a translation reaction liquid is used, the pre-incubation is conducted at about 10 to about 40° C. for about 5 to about 10 minutes, and the incubation in the present reaction (translation reaction) is conducted at about 10 to about 40° C., preferably about 18 to about 30° C., more preferably about 20 to about 26° C. until the reaction stops, usually for about 10 minutes to about 7 hours in a batch method.

When the translation reaction is performed in the double layer method, the protein synthesis is conducted by layering the translation reaction solution containing the biotin derivative and the biotinylating enzyme on the cell extract for protein synthesis to which the crude mRNA or the purified mRNA is added, without disturbing the interface. Specifically, for example, the cell extract for protein synthesis, which may be pre-incubated for a adequate time as occasion demands, is added to the translation template precipitation to dissolve it, resulting in a reaction phase. On the upper layer of the reaction phase, the translation reaction solution (feed phase) is layered without disturbing the interface to react them. The interface between the two phases is not necessary to be formed in a level plane shape, and it is also possible to form the level plane by centrifugation of the mixed liquid containing the two phases. When the diameter of the circular interface of the two phases is 7 mm, the volume ratio of the reaction phase and the feed phase is suitably from 1:4 to 1:8, preferably 1:5. The larger the interface area composed by the two phases, the higher the exchange ratio of the substance due to diffusion and the efficiency of the protein synthesis increase. Thus, the volume ratio of the two phases depends on the interface area between the two phases. In the system using, for instance, a wheat embryo extract, the translation reaction may be conducted under static conditions at about 10 to about 40° C., preferably about 18 to about 30° C., more preferably about 20 to about 26° C., for usually about 10 to about 20 hours. When using the E. coli extract, the reaction temperature is suitably from about 30 to about 37° C.

The detection method by ALPHA using the biotinylated protein obtained in the above-mentioned preparation method of the biotinylated protein will be described below.

The contact reaction of the biotinylated protein, the biological molecule-bonding acceptor beads and the donor beads to which streptavidin is bonded, is performed according to the ALPHA principle. As the solvent, reaction solvents usually used in the interaction between a protein and a biological molecule may be used, and each additive concentration is adjusted to the condition usually used in the interaction between a protein and a biological molecule. In particular, the contact reaction is preferably conducted under conditions of an interaction reaction catalyst and/or an interaction reaction buffer. The reaction is conducted usually at room temperature, suitably about 20 to about 30° C. for about 20 to 150 minutes, preferably about 30 to about 120 minutes.

The interaction between a protein and a biological molecule is detected by the signal change caused by the proximity of the acceptor beads and the donor beads. The detection method of the signal is conducted by, for example, measuring the fluorescence intensity emitted from the acceptor beads.

The method using ALPHA for screening the interaction with the biological molecule in the case where the protein is an autophosphorylated protein, is illustrated as follows:

1) A step for preparing a candidate autophosphorylated protein containing a biotin tag in a wheat embryo cell-free protein synthetic means;

As examples of the candidate autophosphorylated protein, a potential sequence of protein kainase gene is selected from a full length cDNA of mouse which is a mammal model, or a full length cDNA of human and prepared in the wheat embryo cell-free protein synthetic means.

2) A step for preparing a biotinylated candidate autophosphorylated protein by activating a biotinylating enzyme and biotin with a candidate autophosphorylated protein containing a biotin tag;

A gene sequence coding a biotinylating enzyme of E. coli genome is produced with a vector, and the enzyme is prepared in the wheat embryo cell-free protein synthesizing system. However, commercially available biotinylating enzymes may also be used.

3) A step for bonding a phosphorylated detection antibody as the biological molecule directly or indirectly to acceptor beads;

In the direct bonding, the methods known per se can be utilized. In the indirect bonding, an antibody recognizing the biological molecule or protein A can be utilized.

4) A step for detecting phosphorylation in which the biotinylated candidate autophosphorylated protein prepared in the step 2), the acceptor beads prepared in the step 3), and the donor beads to which streptavidin is bonded, are contacted, and the phosphorylation is detected by the signal change caused by the proximity of the acceptor beads and the donor beads Specifically, whether the candidate autophosphorylated protein is autophosphoryled by adding the kination Buffer, or not is confirmed by increase of the signal caused by the proximity of the acceptor beads and the donor beads.

The present invention will be described below in detail by presenting examples, but the scope of the present invention is not limited to these.

EXAMPLE 1

Preparation of Wheat Embryo (1) Preparation of Wheat Embryo

Chihoku wheat seeds of Hokkaido origin, or Chikugo-izumi seeds of Ehime Prefecture origin were added to a mill (supplied by Fritsch Co.: Rotor Speed Millpulverisette type 14) at a rate of 100 g per minute, and the seeds were gently pulverized at 8,000 rpm. After a fraction containing embryo with germinability was recovered with a sieve (mesh size: from 0.7 to 1.00 mm), a floating fraction containing the embryo with germinability was recovered by flotation using a mixture of carbon tetrachloride and cyclohexane (a volume ratio of carbon tetrachloride:cyclohexane=2.4:1), and the organic solvent was removed by drying at room temperature and then contaminating impurities such as seed coat were removed by air blasting at room temperature to give a crude embryo fraction.

Subsequently, using a belt-type color separator BLM-300K (manufacturer: Anzai Manufacturing Co., Ltd., selling agency: Anzai Sogyo), embryo was selected from the crude embryo fraction, utilizing the color difference as below. The color separator comprises means of irradiating light to a crude embryo fraction, means of detecting reflected light and/or transmitted light from the crude embryo fraction, means of comparing the detected value with the standard value, and means of selecting or removing embryos outside the standard value or embryos within the standard value respectively.

The crude embryo fraction was supplied to a beige belt of the color separator at 1000 to 5000 grains/cm$^2$, and the crude embryo fraction on the belt was irradiated with a fluorescent bulb to detect the reflected light. The belt speed was set at 50 m/minute. As a light-receiving sensor, a monochrome CCD line sensor (2048 pixels) was used.

First, in order to remove black components (seed coat and the like) from embryo, a standard value was set between the brightness of the embryo and the brightness of the seed coat, and the components outside the standard value were removed by suction. Next, in order to select endosperm, a standard value was set between the brightness of the embryo and the brightness of the endosperm, and the components outside the standard value were removed by suction. The suction was conducted by using 30 suction nozzles located about 1 cm above the conveying belt (one suction nozzle is arranged per 1 cm length).

The embryo was selected by repeating the procedure until the purity of the embryo (a weight ratio of the embryo per g of an optional sample) reached 98% or more.

The obtained wheat embryo fraction was suspended in distilled water of 4° C., and washed through an ultrasonic washing machine until the cleaning liquid became clear. Subsequently, the resulting product was suspended in a 0.5 volume % solution of Nonidet P40 (supplied by Nakarai Tesque Inc.), and washed through an ultrasonic washing machine until the cleaning liquid became clear to give wheat embryo. An extracting solvent (containing 80 mM of HEPES-KOH (pH 7.8), 200 mM of potassium acetate, 10 mM of magnesium acetate, 8 mM of dithiothreitol, 4 mM of calcium chloride, respectively 0.6 mM of 20 kinds of L-amino acids, and 2.5 mM of ATP) twice the volume of the recovered embryo wet weight was added, and the limited breaking of the embryo was conducted at 5,000 to 20,000 rpm for 30 seconds using a Waring blender three times.

(2) Preparation of S-30 fraction using a precipitating assistant

To the obtained homogenate (broken embryo) as above, beach sand or swollen SEPHADEX™ G25 particles of 20% by weight was added and mixed. The beach sand was previously treated before adding to the homogenate as follows: washing with water→washing with 5 volumes of 0.1 N NaOH or KOH→washing with water→washing with 0.1N HCl→washing with water→inactivation treatment of RNase by heating at 100 to 120° C., and drying treatment.

The homogenate mixed with beach sand was centrifuged at 30000 ×g for 30 minutes twice, followed by once for 12 minutes, resulting in a semi-transparent centrifugation supernatant (S-30 fraction). When the beach sand or the SEPHADEX™ particles were not added before the centrifugation, an insoluble slurry was present on the upper part of the precipitation, and the protein synthesizing activity of the extract prepared from the S-30 fraction containing the slurry was lowered. The obtained S-30 fraction was subjected to the SEPHADEX™ G25 equilibrated with an eluting solution (containing 40 mM of HEPES-KOH (pH 7.8), 200 mM of potassium acetate, 10 mM of magnesium acetate, and 4mM of DTT), and gel filtration was conducted to prepare an embryo extract from which substances with a low molecular weight of not more than 1000 Dalton are excluded.

EXAMPLE 2

Preparation of Biotinylating Enzyme pEU vector to which a base sequence coding a biotinylating enzyme from *E. coli* genome was inserted was prepared. Subsequently, a transcription template was prepared using the pEU vector as a template and using PCR. The transcription template was added to a transcription reaction solution [final concentrations: 80 mM of HEPES-KOH (pH 7.8), 16 mM of magnesium acetate, 10 mM of dithiothreitol, 2 mM of spermidine, 2.5 mM of 4NTPs (4 kinds of nucleotide triphosphates), 0.8 U/μl of RNase inhibitor, and 1.6 U/μl of SP6 RNA polymerase], and the transcription was conducted at 37° C. for 3 hours (Proc Natl Acad Sci USA, 2002, vol 99, p14652-14657: Sawasaki, T et al.). All of the obtained mRNA pellets were added to the wheat embryo extract (200 O.D.) obtained in the above-mentioned Example 1, and the protein synthesis was conducted at 26° C. for 15 to 20 hours.

It was confirmed by using a radio isotope ([$^{14}$C]-Leu) that the above biotinylating enzyme was synthesized.

EXAMPLE 3

Preparation of a Translation Template of Biotinylated Protein (001-006)

In relation to the translation template mRNA, a vector which was a biotinylated protein transcription template in which a gene represented as a gene number of 001-006 was fused with a biotin tag (pEU-biotinylated tag-001-006) was prepared. Based on the vector, a PCR product containing Ω sequence part of tobacco mosaic virus (TMV) was used as a template. The transcription template was added to a transcription reaction solution [final concentrations: 80 mM of HEPES-KOH (pH 7.8), 16 mM of magnesium acetate, 10 mM of dithiothreitol, 2 mM of spermidine, 2.5 mM of 4NTPs (4 kinds of nucleotide triphosphates), 0.8 U/μl of RNase inhibitor, 1.6 U/μl of SP6 RNA polymerase], and the reaction was conducted at 37° C. for 3 hours. The obtained RNA was extracted with phenol/chloroform, precipitated with ethanol, and purified with Nick Column (supplied by Amersham Pharmacia Biotech Inc.) to give a translation template.

As a positive control, a translation template of biotinylated MYT1, biotinylated MST1, biotinylated PKR, biotinylated CK1e, or biotinylated TESK, and as a negative control, a translation template of biotinylated GST was prepared in the same manner as above.

EXAMPLE 4

A Translation Reaction Step of the Biotinylated Protein (001-006) using the Double Layer Method A 96-well titer plate (TPP, Switzerland) was used as a reaction vessel. First, 125.0 µl of the feed phase (2× substrate mixture 62.5 µl, 50 µM biotin of 1.25 µl, and MilliQ 61.25 µl) was added to the titer plate. Next, to 25.0 µl of the reaction phase (4 µg/l creatine kinase of 0.25 µl, the wheat embryo extract (200 O.D.) obtained in Example 1 of 6.5 µl and the biotinylating enzyme (180 O.D.) obtained in Example 2 of 1.0 µl (or O.D 10 (0.8 to 1.5 µM) according to the double layer method of 1.0 µl), 2× substrate mixture of 8.75 µl, 5 µM biotin of 2.5 µl, and MilliQ of 3.5 µl), each translation template (translation template (mRNA) pellets were dissolved in 25 µl of the reaction liquid) obtained in Example 3 was added, and the mixture was added carefully and gently to the bottom of the titer plate. The protein synthesis reaction was conducted under static conditions at 26° C. for 15 to 20 hours.

The synthesized, biotinylated protein was not purified and used in the following Example.

EXAMPLE 5

Detection of the autophosphorylation activity, using ALPHASCREEN™

The reaction liquid of 15 µl (each biotinylated protein obtained in Example 4 (1.0 to 2.0 µl), 5× kination buffer of 3.0 µl, 100 mg/ml BSA of 1.5 µl, 15 µM ATP of 1.0 µl (in case of the detection of the phosphorylation activity of the substrate, ATP was added, but in case of the detection of the autophosphorylation activity, ATP was not added), and MilliQ of 7.5 µl) and 10 µl of a detection liquid (5× kination buffer of 2.0 µl, 100 mg/ml BSA of 1.0 µl, Donor beads of 0.1 µl, Acceptor beads of 0.1 µl, and phosphorylated detecting antibody of 1.0 µl) were mixed and the mixture was allowed to stand at 26° C. for 1 hour, and the fluorescence intensity was measured.

FIG. 1 showing the results of the above-mentioned measurement shows that in the crude proteins 001, 003, and 006, the fluorescence intensity could be detected. Also, in the positive controls, MST1, PKR, CK1e, MYT1 and TESK, the fluorescence intensity could be detected. On the other hand, in the negative control GST, the fluorescence intensity could not be detected. That is, according to the present invention, the autophosphorylation activity of the crude protein can be detected.

EXAMPLE 6

Screening of the autophosphorylated Protein using ALPHASCREEN™

A translation template was prepared in the same manner as in Example 3, and each biotinylated candidate autophosphorylated protein was prepared according to the double layer method in Example 4. 15 µl of a reaction liquid (each biotinylated candidate autophosphorylated protein of 2.0 µl, 5× kination buffer of 3.0 µl, 100 mg/ml BSA of 1.5µl, 15 µM ATP of 1.0 µl and MilliQ of 7.5 µl) and 10 µl of a detecting liquid (5× kination buffer of 2.0 µl, 100 mg/ml BSA of 1.0 µl, Donor beads of 0.1µl, Acceptor beads (phosphorylated detecting antibody was bonded (1600 times of dilution) of 0.1 µl) were mixed, and the mixture was allowed to stand at 26° C. for 1 hour, and the fluorescence intensity was measured.

The results of the above-mentioned measurement newly indicated that AMPKa2, AurB, CaMK1a, CaMK1d, CaMK1g, CaMK4, CCRK, CK1d, CK2a1, DAPK3, DCAMKL3, DYRK1B, eEF2K, GPRK5, GSK3B, MARK1, MELK, MNK1, MPSK1, p38d, PDHK4, PHKg1, PHKg2, PIM2, PIM3, PITSLRE, PKD2, PKD3, PKN2, SgK495, skMLCK, SRPK1, TNK1, Trb2, Trb3 and TSSK2 (SEQ ID NO: 1-36 in order) showed the autophosphorylation activity.

As mentioned above, the biomolecule interaction detection method using the ALPHASCREEN™ of the present invention can be utilized for screening of crude protein autophosphorylating. Further, in the present invention, the protein having the autophosphorylation ability, prepared by the wheat embryo cell-free protein synthetic means could be identified.

Furthermore, the present invention is interested in the following proteins:

1) AMPKa2 represented as SEQ ID NO. 1 which is prepared in a wheat embryo cell-free protein synthetic means and has autophosphorylation ability
2) AurB represented as SEQ ID NO. 2 which is prepared in a wheat embryo cell-free protein synthetic means and has autophosphorylation ability
3) CaMK1a represented as SEQ ID NO. 3 which is prepared in a wheat embryo cell-free protein synthetic means and has autophosphorylation ability
4) CaMK1d represented as SEQ ID NO. 4 which is prepared in a wheat embryo cell-free protein synthetic means and has autophosphorylation ability
5) CaMK1g represented as SEQ ID NO. 5 which is prepared in a wheat embryo cell-free protein synthetic means and has autophosphorylation ability
6) CaMK4 represented as SEQ ID NO. 6 which is prepared in a wheat embryo cell-free protein synthetic means and has autophosphorylation ability
7) CCRK represented as SEQ ID NO. 7 which is prepared in a wheat embryo cell-free protein synthetic means and has autophosphorylation ability
8) CK1d represented as SEQ ID NO. 8 which is prepared in a wheat embryo cell-free protein synthetic means and has autophosphorylation ability
9) CK2a1 represented as SEQ ID NO. 9 which is prepared in a wheat embryo cell-free protein synthetic means and has autophosphorylation ability
10) DAPK3 represented as SEQ ID NO. 10 which is prepared in a wheat embryo cell-free protein synthetic means and has autophosphorylation ability
11) DCAMKL3 represented as SEQ ID NO. 11 which is prepared in a wheat embryo cell-free protein synthetic means and has autophosphorylation ability
12) DYRK1B represented as SEQ ID NO. 12 which is prepared in a wheat embryo cell-free protein synthetic means and has autophosphorylation ability
13) eEF2K represented as SEQ ID NO. 13 which is prepared in a wheat embryo cell-free protein synthetic means and has autophosphorylation ability
14) GPRK5 represented as SEQ ID NO. 14 which is prepared in a wheat embryo cell-free protein synthetic means and has autophosphorylation ability 15) GSK3B represented as SEQ ID NO. 15 which is prepared in a wheat embryo cell-free protein synthetic means and has autophosphorylation ability 16) MARK1 represented as SEQ ID NO. 16 which is prepared in a wheat embryo cell-free protein synthetic means and has autophosphorylation ability
17) MELK represented as SEQ ID NO. 17 which is prepared in a wheat embryo cell-free protein synthetic means and has autophosphorylation ability
18) MNK1 represented as SEQ ID NO. 18 which is prepared in a wheat embryo cell-free protein synthetic means and has autophosphorylation ability
19) MPSK1 represented as SEQ ID NO. 19 which is prepared in a wheat embryo cell-free protein synthetic means and has autophosphorylation ability
20) p38d represented as SEQ ID NO. 20 which is prepared in a wheat embryo cell-free protein synthetic means and has autophosphorylation ability
21) PDHK4 represented as SEQ ID NO. 21 which is prepared in a wheat embryo cell-free protein synthetic means and has autophosphorylation ability
22) PHKg1 represented as SEQ ID NO. 22 which is prepared in a wheat embryo cell-free protein synthetic means and has autophosphorylation ability
23) PHKg2 represented as SEQ ID NO. 23 which is prepared in a wheat embryo cell-free protein synthetic means and has autophosphorylation ability
24) PIM2 represented as SEQ ID NO. 24 which is prepared in a wheat embryo cell-free protein synthetic means and has autophosphorylation ability
25) PIM3 represented as SEQ ID NO. 25 which is prepared in a wheat embryo cell-free protein synthetic means and has autophosphorylation ability
26) PITSLRE represented as SEQ ID NO. 26 which is prepared in a wheat embryo cell-free protein synthetic means and has autophosphorylation ability
27) PKD2 represented as SEQ ID NO. 27 which is prepared in a wheat embryo cell-free protein synthetic means and has autophosphorylation ability
28) PKD3 represented as SEQ ID NO. 28 which is prepared in a wheat embryo cell-free protein synthetic means and has autophosphorylation ability
29) PKN2 represented as SEQ ID NO. 29 which is prepared in a wheat embryo cell-free protein synthetic means and has autophosphorylation ability
30) SgK495 represented as SEQ ID NO. 30 which is prepared in a wheat embryo cell-free protein synthetic means and has autophosphorylation ability
31) skMLCK represented as SEQ ID NO. 31 which is prepared in a wheat embryo cell-free protein synthetic means and has autophosphorylation ability
32) SRPK1 represented as SEQ ID NO. 32 which is prepared in a wheat embryo cell-free protein synthetic means and has autophosphorylation ability
33) TNK1 represented as SEQ ID NO. 33 which is prepared in a wheat embryo cell-free protein synthetic means and has autophosphorylation ability
34) Trb2 represented as SEQ ID NO. 34 which is prepared in a wheat embryo cell-free protein synthetic means and has autophosphorylation ability
35) Trb3 represented as SEQ ID NO. 35 which is prepared in a wheat embryo cell-free protein synthetic means and has autophosphorylation ability
36) TSSK2 represented as SEQ ID NO. 36 which is prepared in a wheat embryo cell-free protein synthetic means and has autophosphorylation ability

INDUSTRIAL APPLICABILITY

The biomolecule interaction detection method using the biotinylated protein obtained in the method for preparing the biotinylated protein according to the present invention allows rapid analysis of polyspecimen, because a step for removing free biotin is not necessary.

What is claimed is:

1. A method for detecting a substance interacting with a protein, wherein a protein with a biotin binding sequence is simultaneously translated and biotinylated using a wheat germ cell-free protein synthesis system in the presence of a biotinylating enzyme and a biotin derivative, and a substance interacting with the biotinylated protein is subsequently detected.

2. The detection method of claim 1, wherein the substance interacting with the biotinylated protein is detected without removing the biotin derivative which was not bound to the protein.

3. The detection method of claim 1, which is at least one selected from 1) amplified luminescence proximity homogenous assay (ALPHA) 2) surface plasmon resonance technique (SPR), 3) fluorescence correlation spectroscopy (FCS), 4) fluorescence intensity distribution analysis (FIDA), 5) enzyme-linked immuno adsorbent assay (ELISA), 6) dissociation enhanced lanthanide fluoro immuno assay (DELFIA), 7) scintillation proximity analysis (SPA), 8) fluorescence resonance energy transfer (FRET), 9) bioluminescent resonance energy transfer (BRET), 10) enzyme fragment complementation (EFC), and 11) fluorescence polarization (FP).

4. The detection method of claim 2, which is at least one selected from 1) ALPHA, 2) SPR, 3) FCS, 4) FIDA, 5) ELISA, 6) DELFIA, 7) SPA, 8) FRET, 9) BRET, 10) EFC, and 11)FP.

5. The detection method of claim 1, wherein the biotinylated protein is fixed to a carrier through a biotin linkage to detect the substance interacting with the biotinylated protein.

6. The detection method of claim 2, wherein the biotinylated protein is fixed to a carrier through a biotin linkage to detect the substance interacting with the biotinylated protein.

7. The detection method of claim 3, wherein the biotinylated protein is fixed to a carrier through a biotin linkage to detect the substance interacting with the biotinylated protein.

8. The detection method of claim 1, wherein the substance interacting with the biotinylated protein is detected using a labeled biotin derivative as a marker.

9. The detection method of claim 2, wherein the substance interacting with the biotinylated protein is detected using a labeled biotin derivative as a marker.

10. The detection method of claim 3, wherein the substance interacting with the biotinylated protein is detected using a labeled biotin derivative as a marker.

11. The detection method of claim 5, wherein the substance interacting with the biotinylated protein is detected using a labeled biotin derivative as a marker.

* * * * *

SEQUENCE LISTING

```
<160> NUMBER OF SEQ ID NOS: 36

<210> SEQ ID NO 1
<211> LENGTH: 1659
<212> TYPE: DNA
<213> ORGANISM: Homo sapiens
<220> FEATURE:
<223> OTHER INFORMATION: AMPKa2

<400> SEQUENCE: 1
atggctgaga agcagaagca cgacgggcgg gtgaagatcg gacactacgt gctgggcgac      60
acgctgggcg tcggcacctt cggcaaagtg aagattggag aacatcaatt aacaggccat     120
aaagtggcag ttaaaatctt aaatagacag aagattcgca gtttagatgt tgttggaaaa     180
ataaaacgag aaattcaaaa tctaaaactc tttcgtcatc ctcatattat caaactatac     240
caggtgatca gcactccaac agattttttt atggtaatgg aatatgtgtc tggaggtgaa     300
ttatttgact acatctgtaa gcatggacgg gttgaagaga tggaagccag gcggctcttt     360
cagcagattc tgtctgctgt ggattactgt cataggcata tggttgttca tcgagacctg     420
aaaccagaga atgtcctgtt ggatgcacac atgaatgcca agatagccga tttcggatta     480
tctaatatga tgtcagatgg tgaatttctg agaactagtt gcggatctcc aaattataca     540
gcacctgaag tcatctcagg cagattgtat gcaggtcctg aagttgatat ctggagctgt     600
```

```
ggtgttatct tgtatgctct tctttgtggc accctcccat tgatgatga gcatgtacct    660 acgttattta agaagatccg aggggggtgtc ttttatatcc agaatatct caatcgttct    720 gtcgccactc tcctgatgca tatgctgcag gttgacccac tgaaacgagc aactatcaaa    780
gacataagag agcatgaatg gtttaaacaa ggtttgccca gttacttatt tcctgaagac    840
ccttcctatg atgctaacgt cattgatgat gaggctgtga agaagtgtg tgaaaaattt    900 gaatgtacag aatcagaagt aatgaacagt ttatatagtg gtgaccctca agaccagctt    960
gcagtggctt atcatcttat cattgacaat cggagaataa tgaaccaagc cagtgagttc   1020
tacctcgcct ctagtcctcc atctggttct tttatggatg atagtgccat gcatattccc   1080
ccaggcctga aacctcatcc agaaaggatg ccacctctta tagcagacag ccccaaagca   1140
agatgtccat tggatgcact gaatacgact aagcccaaat ctttagctgt gaaaaaagcc   1200
aagtggcgtc aaggaatccg aagtcagagc aaaccgtatg acattatggc tgaagtttac   1260
cgagctatga agcagctgga ttttgaatgg aaggtagtga atgcatacca tcttcgtgta   1320
agaagaaaaa atccagtgac tgcaattac gtgaaaatga gcttacaact ttacctggtt   1380
gataacagga gctatctttt ggactttaaa agcattgatg atgaagtagt ggagcagaga   1440
tctggttcct caacacctca gcgttcctgt tctgctgctg gcttacacag accaagatca   1500
agttttgatt ccacaactgc agagagccat tcactttctg gctctctcac tggctctttg   1560
accggaagca cattgtcttc agtttcacct cgcctgggca gtcacaccat ggattttttt   1620
gaaatgtgtg ccagtctgat tactacttta gcccgttga                          1659

<210> SEQ ID NO 2
<211> LENGTH: 1035
<212> TYPE: DNA
<213> ORGANISM: Homo sapiens
<220> FEATURE:
<223> OTHER INFORMATION: AurB

<400> SEQUENCE: 2
atggcccaga aggagaactc ctaccccctgg ccctacggcc gacagacggc tccatctggc     60
ctgagcaccc tgccccagcg agtcctccgg aaagagcctg tcaccccatc tgcacttgtc    120
ctcatgagcc gctccaatgt ccagcccaca gctgccctg gccagaaggt gatggagaat    180
agcagtggga cacccgacat cttaacgcgg cacttcacaa ttgatgactt tgagattggg    240
cgtcctctgg gcaaaggcaa gtttggaaac gtgtacttgg ctcggagaa gaaaagccat    300 ttcatcgtgg cgctcaaggt cctcttcaag tcccagatag agaaggaggg cgtggagcat    360
cagctgcgca gagagatcga aatccaggcc cacctgcacc atcccaacat cctgcgtctc    420
tacaactatt tttatgaccg gaggaggatc tacttgattc tagagtatgc cccccgcggg    480
gagctctaca aggagctgca gaagagctgc acatttgacg agcagcgaac agccacgatc    540
atggaggagt tggcagatgc tctaatgtac tgccatggga agaaggtgat tcacagagac    600
ataaagccag aaaatctgct cttagggctc aaggggagag ctgaagattgc tgacttcggc    660 tggtctgtgc atgcgccctc cctgaggagg aagacaatgt gtggcacccct ggactacctg    720 cccccagaga tgattgaggg cgcatgcac aatgagaagg tggatctgtg gtgcattgga    780
gtgctttgct atgagctgct ggtggggaac ccaccctttg agagtgcatc acacaacgag    840
acctatcgcc gcatcgtcaa ggtggaccta aagttccccg cttctgtgcc cacgggagcc    900
caggacctca tctccaaact gctcaggcat aacccctcgg aacggctgcc cctggcccag    960
```

| | |
|---|---|
| gtctcagccc acccttgggt ccgggccaac tctcggaggg tgctgcctcc ctctgccctt | 1020 |
| caatctgtcg cctga | 1035 |

<210> SEQ ID NO 3
<211> LENGTH: 1113
<212> TYPE: DNA
<213> ORGANISM: Homo sapiens
<220> FEATURE:
<223> OTHER INFORMATION: CaMK1a

<400> SEQUENCE: 3

| | |
|---|---|
| atgctggggg cagtggaagg ccccaggtgg aagcaggcgg aggacattag agacatctac | 60 |
| gacttccgag atgttctggg cacgggggcc ttctcggagg tgatcctggc agaagataag | 120 |
| aggacgcaga agctggtggc catcaaatgc attgccaagg aggccctgga gggcaaggaa | 180 |
| ggcagcatgg agaatgagat tgctgtcctg cacaagatca agcaccccaa cattgtagcc | 240 |
| ctggatgaca tctatgagag tgggggccac ctctacctca tcatgcagct ggtgtcgggt | 300 |
| ggggagctct ttgaccgtat tgtggaaaaa ggcttctaca cggagcggga cgccagccgc | 360 |
| ctcatcttcc aggtgctgga tgctgtgaaa tacctgcatg acctgggcat tgtacaccgg | 420 |
| gatctcaagc cagagaatct gctgtactac agcctggatg aagactccaa aatcatgatc | 480 |
| tccgactttg cctctccaa gatggaggac ccgggcagtg tgctctccac cgcctgtgga | 540 |
| actccgggat acgtggcccc tgaagtcctg gcccagaagc cctacagcaa ggctgtggat | 600 |
| tgctggtcca taggtgtcat cgcctacatc ttgctctgcg gttaccctcc cttctatgac | 660 |
| gagaatgatg ccaaactctt tgaacagatt ttgaaggccg agtacgagtt tgactctcct | 720 |
| tactgggacg acatctctga ctctgccaaa gatttcatcc ggcacttgat ggagaaggac | 780 |
| ccagagaaaa gattcacctg tgagcaggcc ttgcagcacc catggattgc aggagataca | 840 |
| gctctagata gaatatccca ccagtcggtg agtgagcaga tcaagaagaa ctttgccaag | 900 |
| agcaagtgga gcaagccctt caatgccacg gctgtggtgc ggcacatgag gaaactgcag | 960 |
| ctgggcacca gccaggaggg gcaggggcag acggcgagcc atgggagct gctgacacca | 1020 |
| gtggctgggg ggccggcagc tggctgttgc tgtcgagact gctgcgtgga gccgggcaca | 1080 |
| gaactgtccc ccacactgcc ccaccagctc tag | 1113 |

<210> SEQ ID NO 4
<211> LENGTH: 1074
<212> TYPE: DNA
<213> ORGANISM: Homo sapiens
<220> FEATURE:
<223> OTHER INFORMATION: CaMK1d

<400> SEQUENCE: 4

| | |
|---|---|
| atggcccggg agaacggcga gagcagctcc tcctggaaaa agcaagctga agacatcaag | 60 |
| aagatcttcg agttcaaaga accctcggaa accggggcct tttccgaagt ggttttagct | 120 |
| gaagagaagg caactggcaa gctctttgct gtgaagtgta tccctaagaa ggcgctgaag | 180 |
| ggcaaggaaa gcagcataga gaatgagata gccgtcctga aaagattaa gcatgaaaat | 240 |
| attgttgccc tggaagacat ttatgaaagc ccaaatcacc tgtacttggt catgcagctg | 300 |
| gtgtccggtg gagagctgtt tgaccggata tggagaagg ggttttatac agagaaggat | 360 |
| gccagcactc tgatccgcca agtcttggac gccgtgtact atctccacag aatgggcatc | 420 |
| gtccacagag acctcaagcc cgaaaatctc ttgtactaca gtcaagatga ggagtccaaa | 480 |
| ataatgatca gtgactttgg attgtcaaaa atggagggca aaggagatgt gatgtccact | 540 |

-continued

```
gcctgtggaa ctccaggcta tgtcgctcct gaagtcctcg cccagaaacc ttacagcaaa    600
gccgttgact gctggtccat cggagtgatt gcctacatct tgctctgcgg ctaccctcct    660
tttatgatg aaaatgactc caagctcttt gagcagatcc tcaaggcgga atatgagttt     720
gactctccct actgggatga catctccgac tctgcaaaag acttcattcg gaacctgatg    780
gagaaggacc cgaataaaag atacacgtgt gagcaggcag ctcggcaccc atggatcgct    840
ggtgacacag ccctcaacaa aacatccac gagtccgtca gcgcccagat ccggaaaaac     900
tttgccaaga gcaaatggag acaagcattt aatgccacgg ccgtcgtgag acatatgaga    960
aaactacacc tcggcagcag cctggacagt tcaaatgcaa gtgtttcgag cagcctcagt   1020
ttggccagcc aaaaagactg tgcgtatgta gcaaaaccag aatccctcag ctga         1074
```

<210> SEQ ID NO 5
<211> LENGTH: 1431
<212> TYPE: DNA
<213> ORGANISM: Homo sapiens
<220> FEATURE:
<223> OTHER INFORMATION: CaMK1g

<400> SEQUENCE: 5

```
atgggtcgaa aggaagaaga tgactgcagt tcctggaaga acagaccac caacatccgg     60
aaaaccttca tttttatgga agtgctggga tcaggagctt tctcagaagt tttcctggtg    120
aagcaaagac tgactgggaa gctctttgct ctgaagtgca tcaagaagtc acctgccttc    180
cgggacagca gcctggagaa tgagattgct gtgttgaaaa agatcaagca tgaaaacatt    240
gtgaccctgg aggacatcta tgagagcacc accactact acctggtcat gcagcttgtt    300
tctggtgggg agctctttga ccggatcctg agcgggggtg tctacacaga gaaggatgcc    360
agtctggtga tccagcaggt cttgtcggca gtgaataccc tacatgagaa tggcatcgtc    420
cacagagact aaagcccga aaacctgctt taccttaccc ctgaagagaa ctctaagatc    480
atgatcactg actttggtct gtccaagatg gaacagaatg gcatcatgtc cactgcctgt    540
gggaccccag gctacgtggc tccagaagtg ctggcccaga acccctacag caaggctgtg    600
gattgctggt ccatcggcgt catcacctac atattgctct gtggatacc cccattctat    660
gaagaaacgg agtctaagct tttcgagaag atcaaggagg gctactatga gtttgagtct    720
ccattctggg atgacatttc tgagtcagcc aaggacttta tttgccactt gcttgagaag    780
gatccgaacg agcggtacac ctgtgagaag gccttgagtc atccctggat tgacggaaac    840
acagccctcc accgggacat ctacccatca gtcagcctcc agatccagaa gaactttgct   900
aagagcaagt ggaggcaagc cttcaacgca gcagctgtgg tgcaccacat gaggaagcta    960
cacatgaacc tgcacagccc gggcgtccgc ccagaggtgg agaacaggcc gcctgaaact   1020
caagcctcag aaacctctag acccagctcc cctgagatca ccatcaccga ggcacctgtc   1080
ctggaccaca gtgtagcact ccctgccctg acccaattac cctgccagca tggccgccgg   1140
cccactgccc ctggtggcag gtccctcaac tgcctggtca atggctccct ccacatcagc   1200
agcagcctgg tgcccatgca tcaggggtcc ctggccgccg ggccctgtgg ctgctgctcc   1260
agctgcctga acattgggag caaggaaag tcctcctact gctctgagcc cacactcctc     1320
aaaaaggcca acaaaaaaca gaacttcaag tcggaggtca tggtaccagt taaagccagt    1380
ggcagctccc actgccgggc agggcagact ggagtctgtc tcattatgtg a             1431
```

<210> SEQ ID NO 6

<211> LENGTH: 1422
<212> TYPE: DNA
<213> ORGANISM: Homo sapiens
<220> FEATURE:
<223> OTHER INFORMATION: CaMK4

<400> SEQUENCE: 6

```
atgctcaaag tcacggtgcc ctcctgctcc gcctcgtcct gctcttcggt caccgccagt      60
gcggccccgg ggaccgcgag cctcgtcccg gattactgga tcgacggctc caacagggat     120
gcgctgagcg atttcttcga ggtggagtcg gagctggac ggggtgctac atccattgtg     180
tacagatgca aacagaaggg gacccagaag cctatgctc tcaaagtgtt aaagaaaaca     240
gtggacaaaa aaatcgtaag aactgagata ggagttcttc ttcgcctctc acatccaaac     300
attataaaac ttaaagagat atttgaaacc cctacagaaa tcagtctggt cctagaactc     360
gtcacaggag gagaactgtt tgataggatt gtggaaaagg gatattacag tgagcgagat     420
gctgcagatg ccgttaaaca aatcctggag gcagttgctt atctacatga aaatgggatt     480
gtccatcgtg atctcaaacc agagaatctt ctttatgcaa ctccagcccc agatgcacca     540
ctcaaaatcg ctgattttgg actctctaaa attgtgaaac atcaagtgct catgaagaca     600
gtatgtggaa ccccagggta ctgcgcacct gaaattctta gaggttgtgc ctatggacct     660
gaggtggaca tgtggtctgt aggaataatc acctacatct actttgtgg atttgaacca     720
ttctatgatg aaagaggcga tcagttcatg ttcaggagaa ttctgaattg tgaatattac     780
tttatctccc cctggtggga tgaagtatct ctaaatgcca aggacttggt cagaaaatta     840
attgttttgg atccaaagaa acggctgact acatttcaag ctctccagca tccgtgggtc     900
acaggtaaag cagccaattt tgtacacatg gataccgctc aaaagaagct ccaagaattc     960
aatgcccggc gtaagcttaa ggcagcggtg aaggctgtgg tggcctcttc ccgcctggga    1020
agtgccagca gcagccatgg cagcatccag gagagccaca aggctagccg agacccttct    1080
ccaatccaag atggcaacga ggacatgaaa gctattccag aaggagagaa aattcaaggc    1140
gatgggccc aagccgcagt taaggggca caggctgagc tgatgaaggt gcaagcctta    1200
gagaaagtta aggtgcaga tataaatgct gaagaggccc ccaaaatggt gcccaaggca    1260
gtggaggatg ggataaaggt ggctgacctg gaactagagg agggcctagc agaggagaag    1320
ctgaagactg tggaggaggc agcagctccc agagaagggc aaggaagctc tgctgtgggt    1380
tttgaagttc cacagcaaga tgtgatcctg ccagagtact aa                       1422
```

<210> SEQ ID NO 7
<211> LENGTH: 1359
<212> TYPE: DNA
<213> ORGANISM: Homo sapiens
<220> FEATURE:
<223> OTHER INFORMATION: CCRK

<400> SEQUENCE: 7

```
atggaccagt actgcatcct gggccgcatc ggggagggcg cccacggcat cgtcttcaag      60
gccaagcacg tggagactgg cgagataatt gccctcaaga aggtggccct aaggcggttg     120
gaagacggct tccctaacca ggccctgcgg agattaagg ctctgcagga gatggaggac     180
aatcagtatg tggtacaact gaaggctgtg ttcccacacg tggaggctt tgtgctggcc     240
tttgagttca tgctgtcgga tctggccgag gtggtgcgcc atgcccagag gccactagcc     300
caggcacagg tcaagagcta cctgcagatg ctgctcaagg gtgtcgcctt ctgccatgcc     360
aacaacattg tacatcggga cctgaaacct gccaacctgc tcatcagcgc ctcaggccag     420
```

| | |
|---|---|
| ctcaagatag cggactttgg cctggctcga gtcttttccc cagacggcag ccgcctctac | 480 |
| acacaccagg tggccaccag gtctgtgggc tgcatcatgg gggagctgtt gaatgggtcc | 540 |
| cccctttcc cgggcaagaa cgatattgaa cagctttgct atgtgcttcg catcttgggc | 600 |
| acccccaaacc ctcaagtctg gccggagctc actgagctgc cggactacaa caagatctcc | 660 |
| tttaaggagc aggtgcccat gcccctggag gaggtgctgc ctgacgtctc tccccaggca | 720 |
| ttggatctgc tgggtcaatt ccttctctac cctcctcacc agcgcatcgc agcttccaag | 780 |
| gctctcctcc atcagtactt cttcacagct cccctgcctg ccatccatc tgagctgccg | 840 |
| attcctcagc gtctagggg acctgccccc aaggcccatc cagggccccc ccacatccat | 900 |
| gacttccacg tggaccggcc tcttgaggga gtcgctgttg aacccagagc tgattcggcc | 960 |
| cttcatcctg gaggggtgag aagttggccc tggtcccgtc tgcctgctcc tcaggaccac | 1020 |
| tcagtccacc tgttcctctg ccacctgcct ggcttcaccc tccaaggcct ccccatggcc | 1080 |
| acagtgggcc cacaccacac cttgcccctt agcccttgcg agggttggtc tcgaggcaga | 1140 |
| ggtcatgttc ccagccaaga gtatgagaac atccagtcga gcagaggaga ttcatggcct | 1200 |
| gtgctcggtg agccttacct tctgtgtgct actgacgtac ccatcaggac agtgagctct | 1260 |
| gctgccagtc aaggcctgca tatgcagaat gacgatgcct gccttggtgc tgcttccccc | 1320 |
| gagtgctgcc tcctggtcaa ggagaagtgc agagagtaa | 1359 |

<210> SEQ ID NO 8
<211> LENGTH: 1248
<212> TYPE: DNA
<213> ORGANISM: Homo sapiens
<220> FEATURE:
<223> OTHER INFORMATION: CK1d

<400> SEQUENCE: 8

| | |
|---|---|
| atggagctga gagtcgggaa caggtaccgg ctgggccgga agatcggcag cggctccttc | 60 |
| ggagacatct atctcggtac ggacattgct gcaggagaag aggttgccat caagcttgaa | 120 |
| tgtgtcaaaa ccaaacaccc tcagctccac attgagagca aaatctacaa gatgatgcag | 180 |
| ggaggagtgg gcatccccac catcagatgg tgtgggcag aggggactaa caacgtcatg | 240 |
| gtgatggagc tgctggggcc aagcctggag gacctcttca acttctgctc caggaaattc | 300 |
| agcctcaaaa ccgtcctgct gcttgctgac caaatgatca gtcgcatcga atacattcat | 360 |
| tcaaagaact tcatccaccg ggatgtgaag ccagacaact tcctcatggg cctggggaag | 420 |
| aagggcaacc tggtgtacat catcgacttc gggctggcca agaagtaccg ggatgcacgc | 480 |
| acccaccagc acatccccta tcgtgagaac aagaacctca ggggacggc gcggtacgcc | 540 |
| tccatcaaca cgcaccttgg aattgaacaa tcccgaagag atgacttgga gtctctgggc | 600 |
| tacgtgctaa tgtacttcaa cctgggctct ctccccctggc aggggctgaa ggctgccacc | 660 |
| aagagacaga atacgaaag gattagcgag aagaaatgt ccacccccat tgaagtgttg | 720 |
| tgtaaaggct acccttccga atttgccaca tacctgaatt tctgccgttc cttgcgtttt | 780 |
| gacgacaagc ctgactactc gtacctgcgg cagcttttcc ggaatctgtt ccatcgccag | 840 |
| ggcttctcct atgactacgt gttcgactgg aacatgctta aatttggtgc cagccgggcc | 900 |
| gccgatgacg ccgagcggga gcgcagggac cgagaggagc ggctgagaca ctcgcggaac | 960 |
| ccggctaccc gcggcctccc ttccacagac tccggccggc tgcggggac gcaggaagtg | 1020 |
| gctccccca caccctcac ccctacctca cacacggcta acacctcccc ccggcccgtc | 1080 |

-continued

| | |
|---|---|
| tccggcatgg agagagaacg gaaagtgagt atgcggctgc accgcggggc ccccgtcaac | 1140 |
| atctcctcgt ccgacctcac aggccgacaa gataccctc gcatgtccac ctcacagatt | 1200 |
| cctggtcggg tggcttccag tggtcttcag tctgtcgtgc accgatga | 1248 |

<210> SEQ ID NO 9
<211> LENGTH: 1176
<212> TYPE: DNA
<213> ORGANISM: Homo sapiens
<220> FEATURE:
<223> OTHER INFORMATION: CK2a1

<400> SEQUENCE: 9

| | |
|---|---|
| atgtcgggac ccgtgccaag cagggccaga gtttacacag atgttaatac acacagacct | 60 |
| cgagaatact gggattacga gtcacatgtg gtggaatggg gaaatcaaga tgactaccag | 120 |
| ctggttcgaa aattaggccg aggtaaatac agtgaagtat ttgaagccat caacatcaca | 180 |
| aataatgaaa aagttgttgt taaaattctc aagccagtaa aaagaagaa aattaagcgt | 240 |
| gaaataaaga ttttggagaa tttgagagga gtcccaaca tcatcacact ggcagacatt | 300 |
| gtaaaagacc ctgtgtcacg aaccccgcc ttggttttg aacacgtaaa caacacagac | 360 |
| ttcaagcaat tgtaccagac gttaacagac tatgatattc gattttacat gtatgagatt | 420 |
| ctgaaggccc tggattattg tcacagcatg ggaattatgc acagagatgt caagccccat | 480 |
| aatgtcatga ttgatcatga gcacagaaag ctacgactaa tagactgggg tttggctgag | 540 |
| ttttatcatc ctggccaaga atataatgtc cgagttgctt cccgatactt caaaggtcct | 600 |
| gagctacttg tagactatca gatgtacgat tatagtttgg atatgtggag tttgggttgt | 660 |
| atgctggcaa gtatgatctt tcggaaggag ccatttttcc atggacatga caattatgat | 720 |
| cagttggtga ggatagccaa ggttctgggg acagaagatt tatatgacta tattgacaaa | 780 |
| tacaacattg aattagatcc acgtttcaat gatatcttgg gcagacactc tcgaaagcga | 840 |
| tgggaacgct ttgtccacag tgaaaatcag caccttgtca gccctgaggc cttggatttc | 900 |
| ctggacaaac tgctgcgata tgaccaccag tcacggctta ctgcaagaga ggcaatggag | 960 |
| caccctatt tctacactgt tgtgaaggac caggctcgaa tgggttcatc tagcatgcca | 1020 |
| gggggcagta cgcccgtcag cagcgccaat atgatgtcag ggatttcttc agtgccaacc | 1080 |
| ccttcacccc ttggacctct ggcaggctca ccagtgattg ctgctgccaa ccccttggg | 1140 |
| atgcctgttc cagctgccgc tggcgctcag cagtaa | 1176 |

<210> SEQ ID NO 10
<211> LENGTH: 1365
<212> TYPE: DNA
<213> ORGANISM: Homo sapiens
<220> FEATURE:
<223> OTHER INFORMATION: DAPK3

<400> SEQUENCE: 10

| | |
|---|---|
| atgtccacgt tcaggcagga ggacgtggag gaccattatg agatggggga ggagctgggc | 60 |
| agcggccagt ttgcgatcgt gcggaagtgc cggcagaagg gcacgggcaa ggagtacgca | 120 |
| gccaagttca tcaagaagcg ccgcctgtca tccagccggc gtggggtgag ccgggaggag | 180 |
| atcgagcgga aggtgaacat cctgcgggag atccggcacc ccaacatcat caccctgcac | 240 |
| gacatcttcg agaacaagac ggacgtggtc ctcatcctgg agctggtctc tggcggggag | 300 |
| ctctttgact tcctggcgga aaagagtcg ctgacggagg acgaggccac ccagttcctc | 360 |
| aagcagatcc tggacggcgt tcactacctg cactctaagc gcatcgcaca ctttgacctg | 420 |

-continued

```
aagccggaaa acatcatgct gctggacaag aacgtgccca acccacgaat caagctcatc       480
gacttcggca tcgcgcacaa gatcgaggcg gggaacgagt tcaagaacat cttcggcacc       540
ccggagtttg tggccccaga gattgtgaac tatgagccgc tgggcctgga ggcggacatg       600
tggagcatcg tgtcatcac ctatatcctc ctgagcggtg catccccgtt cctgggcgag        660
accaagcagg agacgctcac caacatctca gccgtgaact acgacttcga cgaggagtac       720
ttcagcaaca ccagcgagct ggccaaggac ttcattcgcc ggctgctcgt caaagatccc       780
aagcggagaa tgaccattgc ccagagcctg aacattcct ggattaaggc gatccggcgg        840
cggaacgtgc gtggtgagga cagcggccgc aagcccgagc ggcggcgcct gaagaccacg       900
cgtctgaagg agtacaccat caagtcgcac tccagcttgc cgcccaacaa cagctacgcc       960
gacttcgagc gcttctccaa ggtgctggag gaggcggcgg ccgccgagga gggcctgcgc      1020
gagctgcagc gcagccggcg gctctgccac gaggacgtgg aggcgctggc cgccatctac      1080
gaggagaagg aggcctggta ccgcgaggag agcgacagcc tgggccagga cctgcggagg      1140
ctacggcagg agctgctcaa gaccgaggcg ctcaagcggc aggcgcagga ggaggccaag      1200
ggcgcgctgc tggggaccag cggcctcaag cgccgcttca gccgcctgga gaaccgctac      1260
gaggcgctgg ccaagcaagt agcctccgag atgcgcttcg tgcaggacct cgtgcgcgcc      1320
ctggagcagg agaagctgca gggcgtggag tgcgggctgc gctag                      1365
```

<210> SEQ ID NO 11
<211> LENGTH: 1947
<212> TYPE: DNA
<213> ORGANISM: Homo sapiens
<220> FEATURE:
<223> OTHER INFORMATION: DCAMKL3

<400> SEQUENCE: 11

```
atgggcaaag aaccactgac actgaagagc attcaggtgg ctgtagaaga actgtacccc        60
aacaaagccc gggccctgac actggcccag cacagccgtg cccccttctcc aaggctgagg      120 agcaggctgt ttagcaaggc tctgaaagga gaccaccgct gtggggagac cgagaccccc       180
aagagctgca gcgaagttgc aggatgcaag gcagccatga ggcaccaggg gaagatcccc       240
gaggagcttt cactagatga cagagcgagg acccagaaga agtgggggag ggggaaatgg       300
gagccagaac ccagtagcaa gccccccagg gaagccactc tggaagagag gcacgcaagg      360
ggagagaagc atcttggggt ggagattgaa aagacctcgg gtgaaattat cagatgcgag      420
aagtgcaaga gagagaggga gctccagcag agcctggagc gtgagaggct ttctctgggg      480
accagtgagc tggatatggg gaagggccca atgtatgatg tggagaagct ggtgaggacc      540
agaagctgca ggaggtctcc cgaggcaaat cctgcaagtg gggaggaagg gtggaagggt      600
gacagccaca ggagcagccc caggaatccc actcaagagc tgaggagacc cagcaagagc      660
atggacaaga aagaggacag aggcccagag gatcaagaaa gccatgctca gggagcagcc      720
aaggccaaga aggaccttgt ggaagttctt cctgtcacag aggaggggct gagggaggtg      780
aagaaggaca ccaggcccat gagcaggagc aaacatggtg gctggctcct gagagagcac      840
caggcgggct ttgagaagct ccgcaggacc gaggagaag agaaggaggc agagaaggag       900
aaaaagccat gtatgtctgg aggcagaagg atgactctca gagatgacca acctgcaaag      960
ctagaaaagg agcccaagac gaggccagaa gagaacaagc cagagcggcc cagcggtcgg     1020
aagccacggc ccatgggcat cattgccgcc aatgtggaaa agcattatga gactggccgg     1080
```

```
gtcattgggg atgggaactt tgctgtcgtg aaggagtgca gacaccgcga gaccaggcag    1140
gcctatgcga tgaagatcat tgacaagtcc agactcaagg gcaaggagga catggtggac    1200
agtgagatct tgatcatcca gagcctctct caccccaaca tcgtgaaatt gcatgaagtc    1260
tacgaaacag acatggaaat ctacctgatc ctggagtacg tgcagggagg agaccttttt    1320
gacgccatca tagaaagtgt gaagttcccg gagcccgatg ctgccctcat gatcatggac    1380
ttatgcaaag ccctcgtcca catgcacgac aagagcattg tccaccggga cctcaagccg    1440
gaaaaccttt tggttcagcg aaatgaggac aaatctacta ccttgaaatt ggctgatttt    1500
ggacttgcaa agcatgtggt gagacctata tttactgtgt gtgggacccc aacttacgta    1560
gctcccgaaa ttctttctga gaaggttat ggactggagg tggacatgtg ggctgctggc    1620
gtgatcctct atatcctgct gtgtggcttt cccccattcc gcagccctga gagggaccag    1680
gacgagctct taacatcat ccagctgggc cactttgagt tcctcccccc ttactgggac    1740
aatatctctg atgctgctaa agatctggtg agccggttgc tggtggtaga ccccaaaaag    1800
cgctacacag ctcatcaggt tcttcagcac ccctggatcg aaacagctgg caagaccaat    1860
acagtgaaac gacagaagca ggtgtccccc agcagcgagg gtcacttccg gagccagcac    1920
aagagggttg tggagcaggt atcatag                                        1947

<210> SEQ ID NO 12
<211> LENGTH: 1890
<212> TYPE: DNA
<213> ORGANISM: Homo sapiens
<220> FEATURE:
<223> OTHER INFORMATION: DYRK1B

<400> SEQUENCE: 12
atggccgtcc caccgggcca tggtcccttc tctggcttcc agggccccca ggagcacacg      60
caggtattgc ctgatgtgcg gctactgcct cggaggctgc ccctggcctt ccggatgca     120 acctcagccc cgctgcgtaa gctctctgtg gacctcatca agacctacaa gcacatcaat     180
gaggtatact atgcgaagaa gaagcggcgg cccagcagg cgccaccca ggattcgagc     240 aacaagaagg agaagaaggt cctgaaccat ggttatgatg acgacaacca tgactacatc     300
gtgcgcagtg cgagcgctg gctggagcgc tacgaaattg actcgctcat ggcaaaggc     360 tcctttggcc aggtggtgaa agcctatgat catcagaccc aggagcttgt ggccatcaag     420
atcatcaaga acaaaaaggc tttcctgaac caggcccaga ttgagctgcg gctgctggag     480
ctgatgaacc agcatgacac ggagatgaag tactatatag tacacctgaa gcggcacttc     540
atgttccgga ccaccctgtg cctggtattt gagctgctgt cctacaacct gtacgacctc     600
ctgcgcaaca cccacttccg cggcgtctcg ctgaacctga cccggaagct ggcgcagcag     660
ctctgcacgg cactgctctt tctggccacg cctgagctca gcatcattca ctgcgacctc     720
aagcccgaaa acatcttgct gtgcaacccc aagcgcagcg ccatcaagat gtggacttc     780 ggcagctcct gccagcttgg ccagaggatc taccagtata tccagagccg cttctaccgc     840
tcacctgagg tgctcctggg cacaccctac gacctggcca ttgacatgtg gtccctgggc     900
tgcatccttg tggagatgca caccggagag cccctcttca gtggctccaa tgaggtcgac     960
cagatgaacc gcattgtgga ggtgctgggc atcccaccgg ccgccatgct ggaccaggcg    1020
cccaaggctc gcaagtactt tgaacggctg cctgggggtg gctggaccct acgaaggacg    1080
aaagaactca ggaaggatta ccaggggccc gggacacggc ggctgcagga ggtgctgggc    1140
gtgcagacgg gcgggcccgg gggccggcgg gcggggggagc cgggccacag ccccgccgac    1200
```

-continued

```
tacctccgct tccaggacct ggtgctgcgc atgctggagt atgagcccgc cgcccgcatc    1260
agcccccggg gggctctgca gcacggcttc ttccgccgca cggccgacga ggccaccaac    1320
acgggcccgg caggcagcag tgcctccacc tcgcccgcgc ccctcgacac ctgcccctct    1380
tccagcaccg ccagctccat ctccagttct ggaggctcca gtggctcctc cagtgacaac    1440
cggacctacc gctacagcaa ccgatattgt ggggccctg ggccccctat cacagactgt      1500
gagatgaaca gcccccaggt cccaccctcc cagccgctgc ggccctgggc aggggtgat     1560
gtgcccacaa agacacatca agccctgcc tctgcctcgt cactgcctgg gaccggggcc     1620
cagttaccccc cccagccccg ataccttggt cgtcccccat caccaacctc accaccaccc    1680
ccggagctga tggatgtgag cctggtgggc ggccctgctg actgctcccc acctcaccca    1740
gcgcctgccc ccagcaccc ggctgcctca gccctccgga ctcggatgac tggaggtcgt      1800
ccacccctcc cgcctcctga tgaccctgcc actctggggc ctcacctggg cctccgtggt    1860
gtaccccaga gcacagcagc cagctcgtga                                     1890
```

<210> SEQ ID NO 13
<211> LENGTH: 2178
<212> TYPE: DNA
<213> ORGANISM: Homo sapiens
<220> FEATURE:
<223> OTHER INFORMATION: eEF2K

<400> SEQUENCE: 13

```
atggcagacg aagacctcat cttccgcctg gaaggtgttg atggcggcca gtcccccga      60
gctggccatg atggtgattc tgatggggac agcgacgatg aggaaggtta cttcatctgc    120
cccatcacgg atgacccaag ctcgaaccag aatgtcaatt ccaaggttaa taagtactac    180
agcaacctaa caaaaagtga gcggtatagc tccagcgggt ccccggcaaa ctccttccac    240
ttcaaggaag cctggaagca cgcaatccag aaggccaagc acatgcccga cccctgggct    300
gagttccacc tggaagatat tgccaccgaa cgtgctactc gacacaggta caacgccgtc    360
accggggaat ggctggatga tgaagttctg atcaagatgg catctcagcc cttcggccga    420
ggagcaatga gggagtgctt ccggacgaag aagctctcca acttcttgca tgcccagcag    480
tggaagggcg cctccaacta cgtggcgaag cgctacatcg agcccgtaga ccggggatgtg   540
tactttgagg acgtgcgtct acagatggag gccaagctct gggggagga gtataatcgg    600
cacaagcccc ccaagcaggt ggacatcatg cagatgtgca tcatcgagct gaaggacaga   660
ccgggcaagc ccctcttcca cctggagcac tacatcgagg gcaagtacat caagtacaac   720
tccaactctg gctttgtccg tgatgacaac atccgactga cgccgcaggc cttcagccac   780
ttcactttg agcgttccgg ccatcagctg atagtggtgg acatccaggg agttggggat   840
ctctacactg acccacagat ccacacggag acgggcactg actttggaga cggcaacccta  900
ggtgtccgcg ggatggcgct cttcttctac tctcatgcct gcaaccggat ttgcgagagc    960
atgggccttg ctccctttga cctctcgccc cgggagaggg atgcagtgaa tcagaacacc   1020
aagctgctgc aatcagccaa gaccatcttg agaggaacag aggaaaaatg tgggagcccc   1080
cgagtaagga ccctctctgg agccggcca ccctgctcc gtccccttttc agagaactct   1140
ggagacgaga acatgagcga cgtgaccttc gactctctcc cttcttcccc atcttcggcc   1200
acaccacaca gccagaagct agaccactcc cattggccag tgttcagtga cctcgataac   1260
atggcatcca gagaccatga tcatctagac aaccaccggg agtctgagaa tagtgggggac   1320
```

-continued

```
agcggatacc ccagtgagaa gcggggtgag ctggatgacc ctgagcccg agaacatggc    1380 cactcataca gtaatcggaa gtacgagtct gacgaagaca gcctgggcag ctctggacgg    1440
gtatgtgtag agaagtggaa tctcctcaac tcctcccgcc tccacctgcc gagggcttcg    1500
gccgtggccc tggaagtgca aaggcttaat gctctggacc tcgaaaagaa aatcgggaag    1560
tccattttgg ggaaggtcca tctggccatg gtgcgctacc acgagggtgg gcgcttctgc    1620
gagaagggcg aggagtggga ccaggagtcg gctgtcttcc acctggagca cgcagccaac    1680
ctgggcgagc tggaggccat cgtgggcctg ggactcatgt actcgcagtt gcctcatcac    1740
atcctagccg atgtctctct gaaggagaca gaagagaaca aaaccaaagg atttgattac    1800
ttactaaagg ccgctgaagc tggcgacagg cagtccatga tcctagtggc gcgagctttt    1860
gactctggcc agaacctcag cccggacagg tgccaagact ggctagaggc cctgcactgg    1920
tacaacactg ccctggagat gacggactgt gatgagggcg gtgagtacga cggaatgcag    1980
gacgagcccc ggtacatgat gctggccagg gaggcagaga tgctgttcac aggaggctac    2040
gggctggaga aggacccgca gagatcaggg gacttgtata cccaggcagc agaggcagcg    2100
atggaagcca tgaagggccg actggccaac cagtactacc aaaaggctga agaggcctgg    2160
gcccagatgg aggaataa                                                  2178

<210> SEQ ID NO 14
<211> LENGTH: 1773
<212> TYPE: DNA
<213> ORGANISM: Homo sapiens
<220> FEATURE:
<223> OTHER INFORMATION: GPRK5

<400> SEQUENCE: 14
atggagctgg aaaacatcgt ggccaacacg gtcttgctga agccaggga aggggcgga     60 ggaaagcgca aagggaaaag caagaagtgg aaagaaatcc tgaagttccc tcacattagc    120
cagtgtgaag acctccgaag gaccatagac agagattact gcagtttatg tgacaagcag    180
ccaatcggga ggctgctttt ccggcagttt tgtgaaacca ggcctgggct ggagtgttac    240
attcagttcc tggactccgt ggcagaatat gaagttactc cagatgaaaa actgggagag    300
aaagggaagg aaattatgac caagtacctc accccaaagt ccctgttttt catagcccaa    360
gttggccaag acctggtctc ccagacggag gagaagctcc tacagaagcc gtgcaaagaa    420
ctcttttctg cctgtgcaca gtctgtccac gagtacctga ggggagaacc attccacgaa    480
tatctggaca gcatgttttt tgaccgcttt ctccagtgga gtggttgga aaggcaaccg    540 gtgaccaaaa acactttcag gcagtatcga gtgctaggaa aggggggctt cggggaggtc    600
tgtgcctgcc aggttcgggc cacgggtaaa atgtatgcct gcaagcgctt ggagaagaag    660
aggatcaaaa agaggaaagg ggagtccatg gccctcaatg agaagcagat cctcgagaag    720
gtcaacagtc agtttgtggt caacctggcc tatgcctacg agaccaagga tgcactgtgc    780
ttggtcctga ccatcatgaa tgggggtgac ctgaagttcc acatctacaa catgggcaac    840
cctggcttcg aggaggagcg ggccttgttt tatgcggcag agatcctctg cggcttagaa    900
gacctccacc gtgagaacac cgtctaccga gatctgaaac tgaaaacat cctgttagat    960 gattatggcc acattaggat ctcagacctg ggcttggctg tgaagatccc cgagggagac   1020
ctgatccgcg gccgggtggg cactgttggc tacatggccc ccgaagtcct gaacaaccag   1080
aggtacggcc tgagccccga ctactggggc cttggctgcc tcatctatga gatgatcgag   1140
ggccagtcgc cgttccgcgg ccgtaaggag aaggtgaagc gggaggaggt ggaccgccgg   1200
```

```
gtcctggaga cggaggaggt gtactcccac aagttctccg aggaggccaa gtccatctgc    1260
aagatgctgc tcacgaaaga tgcgaagcag aggctgggct gccaggagga ggggctgca     1320 gaggtcaaga gacaccccct cttcaggaac atgaacttca agcgcttaga agccgggatg    1380
ttggaccctc ccttcgttcc agaccccgc gctgtgtact gtaaggacgt gctggacatc     1440
gagcagttct ccactgtgaa gggcgtcaat ctggaccaca cagacgacga cttctactcc    1500
aagttctcca cgggctctgt gtccatccca tggcaaaacg agatgataga aacagaatgc    1560
tttaaggagc tgaacgtgtt tggacctaat ggtaccctcc cgccagatct gaacagaaac    1620 cacccctccgg aaccgcccaa gaaagggctg ctccagagac tcttcaagcg gcagcatcag   1680
aacaattcca agagttcgcc cagctccaag accagtttta accaccacat aaactcaaac   1740
catgtcagct cgaactccac cggaagcagc tag                                1773
```

<210> SEQ ID NO 15
<211> LENGTH: 1263
<212> TYPE: DNA
<213> ORGANISM: Homo sapiens
<220> FEATURE:
<223> OTHER INFORMATION: GSK3B

<400> SEQUENCE: 15

```
atgtcagggc ggcccagaac cacctccttt gcggagagct gcaagccggt gcagcagcct    60
tcagcttttg gcagcatgaa agttagcaga gacaaggacg gcagcaaggt gacaacagtg    120
gtggcaactc ctgggcaggg tccagacagg ccacaagaag tcagctatac agacactaaa    180
gtgattggaa atggatcatt tggtgtggta tatcaagcca actttgtga ttcaggagaa     240 ctggtcgcca tcaagaaagt attgcaggac aagagattta agaatcgaga gctccagatc    300
atgagaaagc tagatcactg taacatagtc cgattgcgtt atttcttcta ctccagtggt    360
gagaagaaag atgaggtcta tcttaatctg gtgctggact atgttccgga aacagtatac    420
agagttgcca gacactatag tcgagccaaa cagacgctcc ctgtgattta tgtcaagttg    480
tatatgtatc agctgttccg aagtttagcc tatatccatt cctttggaat ctgccatcgg    540
gatattaaac cgcagaacct cttgttggat cctgatactg ctgtattaaa actctgtgac    600
tttggaagtg caaagcagct ggtccgagga gaacccaatg tttcgtatat ctgttctcgg    660
tactataggg caccagagtt gatctttgga gccactgatt atacctctag tatagatgta    720
tggtctgctg gctgtgtgtt ggctgagctg ttactaggac aaccaatatt tccagggga    780 agtggtgtgg atcagttggt agaaataatc aaggtcctgg aactccaac aagggagcaa    840 atcagagaaa tgaacccaaa ctacacagaa tttaaattcc ctcaaattaa ggcacatcct    900
tggactaagg tcttccgacc ccgaactcca ccggaggcaa ttgcactgtg tagccgtctg    960
ctggagtata caccaactgc ccgactaaca ccactggaag cttgtgcaca ttcatttttt    1020
gatgaattac gggacccaaa tgtcaaacat ccaaatgggc gagacacacc tgcactcttc    1080
aacttcacca ctcaagaact gtcaagtaat ccacctctgg ctaccatcct tattcctcct    1140
catgctcgga ttcaagcagc tgcttcaacc cccacaaatg ccacagcagc gtcagatgct    1200
aatactggag accgtggaca gaccaataat gctgcttctg catcagcttc caactccacc    1260
tga                                                                 1263
```

<210> SEQ ID NO 16
<211> LENGTH: 2388
<212> TYPE: DNA

<213> ORGANISM: Homo sapiens
<220> FEATURE:
<223> OTHER INFORMATION: MARK1

<400> SEQUENCE: 16

| | | | | | |
|---|---|---|---|---|---|
| atgtcggccc | ggacgccatt | gccgacggtg | aacgagcggg | acacggtaaa | tcatacgact | 60 |
| gtggatggat | atactgaacc | acacatccag | cctaccaagt | cgagtagcag | acagaacatc | 120 |
| ccccggtgta | gaaactccat | tacgtcagca | acagatgaac | agcctcacat | tggaaattac | 180 |
| cgtttacaaa | aacaatagg | gaagggaaat | tttgccaaag | tcaaattggc | aagacacgtt | 240 |
| ctaactggta | gagaggttgc | tgtgaaaata | atagacaaaa | ctcagctaaa | tcctaccagt | 300 |
| ctacaaaagt | tatttcgaga | agtacgaata | atgaagatac | tgaatcatcc | taatatagta | 360 |
| aaattgtttg | aagttattga | aacagagaag | actctctatt | tagtcatgga | atacgcgagt | 420 |
| gggggtgaag | tatttgatta | cttagttgcc | catggaagaa | tgaaagagaa | agaggcccgt | 480 |
| gcaaaattta | ggcagattgt | atctgctgta | cagtattgtc | atcaaaagta | cattgttcac | 540 |
| cgtgatctta | aggctgaaaa | ccttctcctt | gatggtgata | tgaatattaa | aattgctgac | 600 |
| tttggtttta | gtaatgaatt | tacagttggg | aacaaattgg | acacattttg | tggaagccca | 660 |
| ccctatgctg | ctcccgagct | tttccaagga | agaagtatg | atgggcctga | agtggatgtg | 720 |
| tggagtctgg | gcgtcattct | ctatacatta | gtcagtggct | ccttgccttt | cgatggccag | 780 |
| aatttaaagg | aactgcgaga | gcgagtttta | cgagggaagt | accgtattcc | cttctatatg | 840 |
| tccacagact | gtgaaaatct | tctgaagaaa | ttattagtcc | tgaatccaat | aaagagaggc | 900 |
| agcttggaac | aaataatgaa | agatcgatgg | atgaatgttg | gtcatgaaga | ggaagaacta | 960 |
| aagccatata | ctgagcctga | tccggatttc | aatgacacaa | aagaatagaa | cattatggtc | 1020 |
| accatgggct | ttgcacgaga | tgaaataaat | gatgccttaa | taaatcagaa | gtatgatgaa | 1080 |
| gttatggcta | cttatattct | tctaggtaga | aaaccacctg | aatttgaagg | tggtgaatcg | 1140 |
| ttatccagtg | gaaacttgtg | tcagaggtcc | cggcccagta | gtgacttaaa | caacagcact | 1200 |
| cttcagtccc | ctgctcacct | gaaggtccag | agaagtatct | cagcaaatca | gaagcagcgg | 1260 |
| cgtttcagtg | atcatgctgg | tccatccatt | cctcctgctg | tatcatatac | caaaagacct | 1320 |
| caggctaaca | gtgtggaaag | tgaacagaaa | gaggagtggg | acaaagatgt | ggctcgaaaa | 1380 |
| cttggcagca | caacagttgg | atcaaaaagc | gagatgactg | caagccctct | tgtagggcca | 1440 |
| gagaggaaaa | aatcttcaac | tattccaagt | aacaatgtgt | attctggagg | tagcatggca | 1500 |
| agaaggaata | catatgtctg | tgaaaggacc | acagatcgat | acgtagcatt | gcagaatgga | 1560 |
| aaagacagca | gccttacgga | gatgtctgtg | agtagcatat | cttctgcagg | ctcttctgtg | 1620 |
| gcctctgctg | tccctcagc | acgacccgc | accagaagt | ccatgtccac | ttctggtcat | 1680 |
| cctattaaag | tcacactgcc | aaccattaaa | gacggctctg | aagcttaccg | gcctggtaca | 1740 |
| acccagagag | tgcctgctgc | ttccccatct | gctcacagta | ttagtactgc | gactccagac | 1800 |
| cggacccgtt | ttccccgagg | gagctcaagc | cgaagcactt | tccatggtga | acagctccgg | 1860 |
| gagcgacgca | gcgttgctta | taatgggcca | cctgcttcac | catcccatga | aacgggtgca | 1920 |
| tttgcacatg | ccagaagggg | aacgtcaact | ggtataataa | gcaaaatcac | atccaaattt | 1980 |
| gttcgcagga | atccaagtga | aggcgaagcc | agtggcagaa | ccgacacctc | aagaagtaca | 2040 |
| tcagggaac | caaaagaaag | agacaaggaa | gagggtaaag | attctaagcc | gcgttctttg | 2100 |
| cggttcacat | ggagtatgaa | gaccactagt | tcaatggacc | ctaatgacat | gatgagagaa | 2160 |
| atccgaaaag | tgttagatgc | aaataactgt | gattatgagc | aaaaagagag | atttttgctt | 2220 |

```
ttctgtgtcc atggagacgc tagacaggat agcctcgtgc agtgggagat ggaagtctgc    2280
aagttgccac gactgtcact taatgggggtt cgcttcaagc gaatatctgg gacatctatt   2340
gcctttaaga acattgcatc aaaaatagca aatgagctta agctgtaa                 2388

<210> SEQ ID NO 17
<211> LENGTH: 1956
<212> TYPE: DNA
<213> ORGANISM: Homo sapiens
<220> FEATURE:
<223> OTHER INFORMATION: MELK

<400> SEQUENCE: 17
atgaaagatt atgatgaact tctcaaatat tatgaattac atgaaactat tgggacaggt      60
ggctttgcaa aggtcaaact tgcctgccat atccttactg gagagatggt agctataaaa    120
atcatggata aaacacact agggagtgat ttgccccgga tcaaaacgga gattgaggcc     180
ttgaagaacc tgagacatca gcatatatgt caactctacc atgtgctaga gacagccaac    240
aaaatattca tggttcttga gtactgcccct ggaggagagc tgtttgacta tataatttcc   300
caggatcgcc tgtcagaaga ggagacccgg gttgtcttcc gtcagatagt atctgctgtt   360
gcttatgtgc acagccaggg ctatgctcac agggacctca agccagaaaa tttgctgttt   420
gatgaatatc ataaattaaa gctgattgac tttggtctct gtgcaaaacc caagggtaac   480
aaggattacc atctacagac atgctgtggg agtctggctt atgcagcacc tgagttaata   540
caaggcaaat catatcttgg atcagaggca atgtttggga catgggcat actgttatat   600 gttcttatgt gtggatttct accatttgat gatgataatg taatggcttt atacaagaag   660
attatgagag gaaatatga tgttcccaag tggctctctc ccagtagcat tctgcttctt   720
caacaaatgc tgcaggtgga cccaaagaaa cggatttcta tgaaaaatct attgaaccat   780
ccctggatca tgcaagatta caactatcct gttgagtggc aaagcaagaa tcctttttatt   840 cacctcgatg atgattgcgt aacagaactt tctgtacatc acagaaacaa caggcaaaca   900
atggaggatt taatttcact gtggcagtat gatcacctca cggctaccta tcttctgctt   960
ctagccaaga aggctcgggg aaaaccagtt cgtttaaggc tttcttcttt ctcctgtgga   1020
caagccagtc taccccatt cacagacatc aagtcaaata attggagtct ggaagatgtg   1080
accgcaagtg ataaaaatta tgtggcggga ttaatagact atgattggtg tgaagatgat   1140
ttatcaacag gtgctgctac tccccgaaca tcacagttta ccaagtactg gacagaatca   1200 aatgggggtgg aatctaaatc attaactcca gccttatgca gaacacctgc aaataaatta   1260
aagaacaaag aaaatgtata tactcctaag tctgctgtaa agaatgaaga gtactttatg   1320
tttcctgagc caaagactcc agttaataag aaccagcata gagagaaat actcactacg   1380 ccaaatcgtt acactacacc ctcaaaagct agaaaccagt gcctgaaaga aactccaatt   1440
aaaataccag taaattcaac aggaacagac aagttaatga caggtgtcat tagccctgag   1500
aggcggtgcc gctcagtgga attggatctc aaccaagcac atatggagga gactccaaaa   1560
agaaagggag ccaaagtgtt tgggagcctt gaaaggggggt tggataaggt tatcactgtg   1620
ctcaccagga gcaaaggaa gggttctgcc agagacgggc ccagaagact aaagcttcac   1680
tataatgtga ctacaactag attagtgaat ccagatcaac tgttgaatga aataatgtct   1740
attcttccaa agaagcatgt tgactttgta caaaagggtt atacactgaa gtgtcaaaca   1800
cagtcagatt ttgggaaagt gacaatgcaa tttgaattag aagtgtgcca gcttcaaaaa   1860
```

```
cccgatgtgg tgggtatcag gaggcagcgg cttaagggcg atgcctgggt ttacaaaaga   1920
ttagtggaag acatcctatc tagctgcaag gtataa                            1956

<210> SEQ ID NO 18
<211> LENGTH: 1275
<212> TYPE: DNA
<213> ORGANISM: Homo sapiens
<220> FEATURE:
<223> OTHER INFORMATION: MNK1

<400> SEQUENCE: 18
atggtatctt ctcaaaagtt ggaaaaacct atagagatgg gcagtagcga accccttccc     60
atcgcagatg gtgacaggag gaggaagaag aagcggaggg ccgggccac tgactccttg    120 ccaggaaagt ttgaagatat gtacaagctg acctctgaat tgcttggaga gggagcctat   180
gccaaagttc aaggtgccgt gagcctacag aatggcaaag agtatgccgt caaaatcatc   240
gagaaacaag cagggcacag tcggagtagg gtgtttcgag aggtggagac gctgtatcag   300
tgtcagggaa acaagaacat tttggagctg attgagttct ttgaagatga cacaaggttt   360
tacttggtct ttgagaaatt gcaaggaggt tccatcttag cccacatcca gaagcaaaag   420
cacttcaatg agcgagaagc cagccgagtg gtgcgggacg ttgctgctgc ccttgacttc   480
ctgcatacca aaggcattgc tcatcgtgat ctgaaaccag aaaatatatt gtgtgaatct   540
ccagaaaagg tgtctccagt gaaaatctgt gactttgact gggcagtgg atgaaactg    600 aacaactcct gtaccccat aaccacacca gagctgacca ccccatgtgg ctctgcagaa   660
tacatggccc ctgaggtagt ggaggtcttc acggaccagg ccacattcta cgacaagcgc   720
tgtgacctgt ggagcctggg cgtggtcctc tacatcatgc tgagtggcta cccacccttc   780
gtgggtcact gcggggccga ctgtggctgg accggggcg aggtctgcag ggtgtgccag   840
aacaagctgt ttgaaagcat ccaggaaggc aagtatgagt ttcctgacaa ggactgggca   900
cacatctcca gtgaagccaa agacctcatc tccaagctcc tggtgcgaga tgcaaagcag   960
agacttagcg ccgcccaagt tctgcagcac ccatgggtgc aggggcaagc tccagaaaag  1020
ggactcccca cgccgcaagt cctccagagg aacagcagca caatggacct gacgctcttc  1080
gcagctgagg ccatcgccct taaccgccag ctatctcagc acgaagagaa cgaactagca  1140
gaggagccag aggcactagc tgatggcctc tgctccatga gctttccccc tcctgcaag   1200 tcacgcctgg cccggagacg ggccctggcc caggcaggcc gtggtgaaga caggagcccg  1260
cccacagcac tctga                                                   1275

<210> SEQ ID NO 19
<211> LENGTH: 918
<212> TYPE: DNA
<213> ORGANISM: Homo sapiens
<220> FEATURE:
<223> OTHER INFORMATION: MPSK1

<400> SEQUENCE: 19
atgggccacg cgctgtgtgt ctgctctcgg ggaactgtca tcattgacaa taagcgctac     60
ctcttcatcc agaaactggg ggagggtggg ttcagctatg tggacctagt ggaagggtta   120
catgatggac acttctacgc cctgaagcga atcctgtgtc acgagcagca ggaccgggag   180
gaggcccagc gagaagccga catgcatcgc ctcttcaatc accccaacat ccttcgcctc   240
gtggcttact gtctgagggg acggggtgct aagcatgagg cctggctgct gctaccattc   300
ttcaagagag gtacgctgtg gaatgagata gaaaggctga aggacaaagg caacttcctg   360
```

```
accgaggatc aaatcctttg gctgctgctg gggatctgca gaggccttga ggccattcat   420
gccaagggtt atgcccacag agacttgaag cccaccaata tattgcttgg agatgagggg   480
cagccagttt aatggacttg ggttccatga atcaagcatg catccatgtg gagggctcc    540 cgccaggctc tgaccctgca ggactgggca gcccagcggt gcaccatctc ctaccgagcc   600
ccagagctct tctctgtgca gagtcactgt gtcatcgatg agcggactga tgtctggtcc   660
tttggctgcg tgctatatgc catgatgttt ggggaaggcc ttatgacat ggtgttccaa    720 aagggtgaca gtgtggccct tgctgtgcag aaccaactca gcatcccaca aagccccagg   780
cattcttcag cattgcggca gctcctgaac tcgatgatga ccgtggaccc gcatcagcgt   840
cctcacattc ctctcctcct cagtcagctg gaggcgctgc agccccagc tcctggccaa    900 catactaccc aaatctga                                                  918

<210> SEQ ID NO 20
<211> LENGTH: 1098
<212> TYPE: DNA
<213> ORGANISM: Homo sapiens
<220> FEATURE:
<223> OTHER INFORMATION: p38d

<400> SEQUENCE: 20
atgagcctca tccggaaaaa gggcttctac aagcaggacg tcaacaagac cgcctgggag    60
ctgcccaaga cctacgtgtc cccgacgcac gtcggcagcg gggcctatgg ctccgtgtgc   120
tcggccatcg acaagcggtc aggggagaag gtggccatca agaagctgag ccgacccttt   180
cagtccgaga tcttcgccaa gcgcgcctac cgggagctgc tgctgctgaa gcacatgcag   240
catgagaacg tcattgggct cctggatgtc ttcacccag cctcctccct gcgcaacttc    300
tatgacttct acctggtgat gccttcatg cagacggatc tgcagaagat catggggatg   360
gagttcagtg aggagaagat ccagtacctg gtgtatcaga tgctcaaagg ccttaagtac   420
atccactctg ctggggtcgt gcacagggac ctgaagccag caacctggc tgtgaatgag    480 gactgtgaac tgaagattct ggattttggg ctggcgcgac atgcagacgc cgagatgact   540
ggctacgtgg tgacccgctg gtaccgagcc cccgaggtga tcctcagctg gatgcactac   600
aaccagacag tggacatctg gtctgtgggc tgtatcatgg cagagatgct gacagggaaa   660
actctgttca agggaaaga ttacctggac cagctgaccc agatcctgaa agtgaccggg    720
gtgcctggca cggagtttgt gcagaagctg aacgacaaag cggccaaatc ctacatccag   780
tccctgccac agacccccag gaaggatttc actcagctgt cccacgggc agccccag     840 gctgcggacc tgctggagaa gatgctggag ctagacgtgg acaagcgcct gacggccgcg   900
caggccctca cccatccctt ctttgaaccc ttccgggacc ctgaggaaga cggaggcc    960 cagcagccgt tgatgattc cttagaacac gagaaactca cagtggatga atggaagcag   1020
cacatctaca aggagattgt gaacttcagc cccattgccc ggaaggactc acggcgccgg   1080
agtggcatga agctgtag                                                1098

<210> SEQ ID NO 21
<211> LENGTH: 1236
<212> TYPE: DNA
<213> ORGANISM: Homo sapiens
<220> FEATURE:
<223> OTHER INFORMATION: PDHK4

<400> SEQUENCE: 21
```

```
atgaaggcgg cccgcttcgt gctgcgcagc gctggctcgc tcaacggcgc cggcctggtg     60 cccccgagagg tggagcattt ctcgcgctac agcccgtccc cgctgtccat gaagcagcta    120
ctggactttg gttcagaaaa tgcatgtgaa agaacttctt ttgcattttt gcgacaagaa    180
ttgcctgtga gactcgccaa cattctgaag gaaattgata tcctcccgac ccaattagta    240
aatacctctt cagtgcaatt ggttaaaagc tggtatatac agagcctgat ggatttggtg    300
gaattccatg agaaaagccc agatgaccag aaagcattat cagactttgt agatacactc    360
atcaaagttc gaaatagaca ccataatgta gtccctacaa tggcacaagg aatcatagag    420
tataaagatg cctgtacagt tgacccagtc accaatcaaa tcttcaata tttcttggat     480 cgattttaca tgaaccgtat ttctactcgg atgctgatga accagcacat tcttatattt    540
agtgactcac agacaggaaa cccaagccac attggaagca ttgatcctaa ctgtgatgtg    600
gtagcagtgg tccaagatgc ctttgagtgt caaggatgc tctgtgatca gtattattta    660
tcatctccag aattaaagct tacacaagtg aatggaaaat ttccagacca accaattcac    720
atcgtgtatg ttccttctca cctccatcat atgctctttg aactatttaa gaatgcaatg    780
cgggcaacag ttgaacacca ggaaaatcag ccttccctta caccaataga ggttattgtt    840
gtcttgggaa agaagacct taccattaag atttcagaca gaggaggtgg tgttcccctg    900
agaattattg accgcctctt tagttataca tactccactg caccaacgcc tgtgatggat    960
aattcccgga atgctccttt ggctggtttt ggttacggct tgccaatttc tcgtctgtat   1020
gcaaagtact ttcaaggaga tctgaatctc tactctttat caggatatgg aacagatgct   1080
atcatctact taaaggcttt gtcttctgag tctatagaaa aacttccagt ttttaacaag   1140
tcagccttca acattatca gatgagctct gaggctgatg actggtgtat cccaagcagg   1200
gaaccaaaga acctggcaaa agaagtggcc atgtga                             1236
```

<210> SEQ ID NO 22
<211> LENGTH: 1164
<212> TYPE: DNA
<213> ORGANISM: Homo sapiens
<220> FEATURE:
<223> OTHER INFORMATION: PHKg1

<400> SEQUENCE: 22

```
atgacccggg acgaggcact gccggactct cattctgcac aggacttcta tgagaattat     60
gagcccaaag agatcctggg caggggcgtt agcagtgtgg tcaggcgatg catccacaag    120
cccacgagcc aggagtacgc cgtgaaggtc atcgacgtca ccggtggagg cagcttcagc    180
ccggaggagg tgcgggagct gcgagaagcc acgctgaagg aggtggacat cctgcgcaag    240
gtctcagggc accccaacat catacagctg aaggacactt atgagaccaa cacttctctc    300
ttcttggtgt ttgacctgat gaagagaggg gagctctttg actacctcac tgagaaggtc    360
accttgagtg agaaggaaac cagaaagatc atgcgagctc tgctggaggt gatctgcacc    420
ttgcacaaac tcaacatcgt gcaccgggac ctgaagcccg agaacattct cttggatgac    480
aacatgaaca tcaagctcac agactttggc ttttcctgcc agctggagcc gggagagagg    540
ctgcgagagg tctgcgggac ccccagttac ctggcccctg agattatcga gtgctccatg    600
aatgaggacc acccgggcta cgggaaagag gtggacatgt ggagcactgg cgtcatcatg    660
tacacgctgc tggccggctc cccgcccttc tggcaccgga agcagatgct gatgctgagg    720
atgatcatga gcggcaacta ccagtttggc tcgcccgagt gggatgatta tcggacacc    780 gtgaaggacc tggtctcccg attcctggtg gtgcaacccc agaaccgcta cacagcggaa   840
```

```
gaggccttgg cacaccccttc ttccagcag tacttggtgg aggaagtgcg gcacttcagc    900 ccccgggggga agttcaaggt gatcgctctg accgtgctgg cttcagtgcg gatctactac    960
cagtaccgcc gggtgaagcc tgtgacccgg gagatcgtca tccgagaccc ctatgccctc   1020
cggcctctgc gccggctcat cgacgcctac gctttccgaa tctatggcca ctgggtgaag   1080 aagggggcagc agcagaaccg ggcagcccct ttcgagaaca cacccaaggc cgtgctcctc   1140
tccctggccg aggaggacta ctga                                           1164
```

<210> SEQ ID NO 23
<211> LENGTH: 1221
<212> TYPE: DNA
<213> ORGANISM: Homo sapiens
<220> FEATURE:
<223> OTHER INFORMATION: PHKg2

<400> SEQUENCE: 23

```
atgacgctgg acgtggggcc ggaggatgag ctgcccgact gggccgccgc caaagagttt     60
taccagaagt acgaccctaa ggacgtcatc ggcagaggag tgagctctgt ggtccgccgt    120
tgtgttcatc gagctactgg ccacgagttt gcggtgaaga ttatggaagt gacagctgag    180
cggctgagtc ctgagcagct ggaggaggtg cgggaagcca cacggcgaga gacacacatc    240
cttcgccagg tcgccggcca ccccacatc atcaccctca tcgattccta cgagtcttct     300
agcttcatgt tcctggtgtt tgacctgatg cggaagggag agctgtttga ctatctcaca    360
gagaaggtgg ccctctctga aaaggaaacc aggtccatca tgcggtctct gctgaagca     420 gtgagctttc tccatgccaa caacattgtg catcgagatc tgaagcccga aatattctc     480 ctagatgaca atatgcagat ccgactttca gatttcgggt tctcctgcca cttggaacct    540
ggcgagaagc ttcgagagtt gtgtgggacc ccagggtatc tagcgccaga gatccttaaa    600
tgctccatgg atgaaaccca cccaggctat ggcaaggagg tcgacctctg gcctgtggg    660 gtgatcttgt tcacactcct ggctggctcg ccacccttct ggcaccggcg gcagatcctg    720
atgttacgca tgatcatgga gggccagtac cagttcagtt ccccgagtg ggatgaccgt     780 tccagcactg tcaaagacct gatctccagg ctgctgcagg tggatcctga ggcacgcctg    840
acagctgagc aggccctaca gcaccccttc tttgagcgtt gtgaaggcag ccaaccctgg    900
aacctcaccc ccgccagcg gttccgggtg gcagtgtgga cagtgctggc tgctggacga    960
gtggccctaa gcaccatcg tgtacggcca ctgaccaaga atgcactgtt gagggacct   1020 tatgcgctgc ggtcagtgcg gcacctcatc gacaactgtg ccttccggct ctacgggcac   1080
tgggtaaaga aagggggagca gcagaaccgg cggctctct ttcagcaccg gccccctggg   1140 cctttttccca tcatgggccc tgaagaggag ggagactctg ctgctataac tgaggatgag   1200
gccgtgcttg tgctgggcta g                                             1221
```

<210> SEQ ID NO 24
<211> LENGTH: 1005
<212> TYPE: DNA
<213> ORGANISM: Homo sapiens
<220> FEATURE:
<223> OTHER INFORMATION: PIM2

<400> SEQUENCE: 24

```
atgttgacca agcctctaca ggggcctccc gcgcccccccg gaccccccac gccgccgcca     60
ggaggcaagg atcgggaagc gttcgaggcc gagtatcgac tcggccccct cctgggtaag    120
```

```
gggggctttg gcaccgtctt cgcaggacac cgcctcacag atcgactcca ggtggccatc      180
aaagtgattc cccggaatcg tgtgctgggc tggtcccect tgtcagactc agtcacatgc      240
ccactcgaag tcgcactgct atggaaagtg ggtgcaggtg gtgggcaccc tggcgtgatc      300
cgcctgcttg actggtttga cacacaggaa ggcttcatgc tggtcctcga gcggcctttg      360
cccgcccagg atctctttga ctatatcaca gagaagggcc cactgggtga aggcccaagc      420
cgctgcttct ttggccaagt agtggcagcc atccagcact gccattcccg tggagttgtc      480
catcgtgaca tcaaggatga gaacatcctg atagacctac gccgtggctg tgccaaactc      540
attgattttg gttctggtgc cctgcttcat gatgaaccct acactgactt tgatgggaca      600
agggtgtaca gcccccaga gtggatctct cgacaccagt accatgcact cccggccact       660
gtctggtcac tgggcatcct cctctatgac atggtgtgtg gggacattcc ctttgagagg      720
gaccaggaga ttctggaagc tgagctccac ttcccagccc atgtctcccc agactgctgt      780
gccctaatcc gccggtgcct ggcccccaaa ccttcttccc gacccteact ggaagagatc      840 ctgctggacc cctggatgca aacaccagcc gaggatgtta cccctcaacc cctccaaagg      900
aggccctgcc cctttggcct ggtccttgct accctaagcc tggcctggcc tggcctggcc      960
cccaatggtc agaagagcca tcccatggcc atgtcacagg gatag                    1005

<210> SEQ ID NO 25
<211> LENGTH: 981
<212> TYPE: DNA
<213> ORGANISM: Homo sapiens
<220> FEATURE:
<223> OTHER INFORMATION: PIM3

<400> SEQUENCE: 25
atgctgctct ccaagttcgg ctccctggcg cacctctgcg ggcccggcgg cgtggaccac       60
ctcccggtga agatcctgca gccagccaag gcggacaagg agagcttcga gaaggcgtac      120
caggtgggcg ccgtgctggg tagcggcggc ttcggcacgg tctacgcggg tagccgcatc      180
gccgacgggc tcccggtggc tgtgaagcac gtggtgaagg agcgggtgac cgagtggggc      240
agcctgggcg gcgcgaccgt gcccctggag gtggtgctgc tgcgcaaggt gggcgcggcg      300
ggcggcgcgc gcggcgtcat ccgcctgctg gactggttcg agcggcccga cggcttcctg      360
ctggtgctgg agcggcccga gccggcgcag gacctcttcg actttatcac ggagcgcggc      420
gccctggacg agccgctggc gcgccgcttc ttcgcgcagg tgctggccgc cgtgcgccac      480
tgccacagct gcggggtcgt gcaccgcgac attaaggacg aaaatctgct tgtggacctg      540
cgctccggag agctcaagct catcgacttc ggttcgggtg cgctgctcaa ggacacggtc      600
tacaccgact tcgacggcac ccgagtgtac agcccccgg agtggatccg ctaccaccgc      660
taccacgggc gctcggccac cgtgtggtcg ctgggcgtgc ttctctacga tatggtgtgt      720
ggggacatcc ccttcgagca ggacgaggag atcctccgag gccgcctgct cttccggagg      780
agggtctctc cagagtgcca gcagctgatc cggtggtgcc tgtccctgcg gcoctcagag      840 cggccgtcgc tggatcagat tgcggcccat ccctggatgc tggggctga cggggcgcc       900 ccggagagct gtgacctgcg gctgtgcacc ctcgaccctg atgacgtggc cagcaccacg      960
tccagcagcg agagcttgtg a                                                981

<210> SEQ ID NO 26
<211> LENGTH: 1320
<212> TYPE: DNA
<213> ORGANISM: Homo sapiens
```

<220> FEATURE:
<223> OTHER INFORMATION: PITSLRE

<400> SEQUENCE: 26

| | | | | | |
|---|---|---|---|---|---|
| atgagtgaag | atgaagaacg | agaaaatgaa | aaccacctct | tggttgttcc | agagtcacgg | 60 |
| ttcgaccgag | attccgggga | gagtgaagaa | gcagaggaag | aagtgggtga | gggaacgccg | 120 |
| cagagcagcg | ccctgacaga | gggcgactat | gtgcccgact | cccctgccct | gtcgccatc | 180 |
| gagctcaagc | aggagctgcc | caagtacctg | ccggccctgc | agggctgccg | gagcgtcgag | 240 |
| gagttccagt | gcctgaacag | gatcgaggag | ggcacctatg | gagtggtcta | cagagcaaaa | 300 |
| gacaagaaaa | cagatgaaat | tgtggctcta | aagcggctga | agatggagaa | ggagaaggag | 360 |
| ggcttcccga | tcacgtcgct | gagggagatc | aacaccatcc | tcaaggccca | gcatcccaac | 420 |
| atcgtcaccg | ttagagagat | tgtggtgggc | agcaacatgg | acaagatcta | catcgtgatg | 480 |
| aactatgtgg | agcacgacct | caagagcctg | atggagacca | tgaaacagcc | cttcctgcca | 540 |
| ggggaggtga | agaccctgat | gatccagctg | ctgcgtgggg | tgaaacacct | gcacgacaac | 600 |
| tggatcctgc | accgtgacct | caagacgtcc | aacctgctgc | tgagccacgc | cggcatcctc | 660 |
| aaggtgggtg | acttcgggct | ggcgcgggag | tacggatccc | ctctgaaggc | ctacaccccg | 720 |
| gtcgtggtga | ccctgtggta | ccgcgcccca | gagctgctgc | ttggtgccaa | ggaatactcc | 780 |
| acggccgtgg | acatgtggtc | agtgggttgc | atcttcgggg | agctgctgac | tcagaagcct | 840 |
| ctgttccccg | gaagtcaga | aatcgatcag | atcaacaagg | tgttcaagga | tctggggacc | 900 |
| cctagtgaga | aaatctggcc | cggctacagc | gagctcccag | cagtcaagaa | gatgaccttc | 960 |
| agcgagcacc | cctacaacaa | cctccgcaag | cgcttcgggg | ctctgctctc | agaccagggc | 1020 |
| ttcgacctca | tgaacaagtt | cctgacctac | ttccccggga | ggaggatcag | cgctgaggac | 1080 |
| ggcctcaagc | atgagtattt | ccgcgagacc | cccctcccca | tcgacccctc | catgttcccc | 1140 |
| acgtggcccg | ccaagagcga | gcagcagcgt | gtgaagcggg | gcaccagccc | gaggcccct | 1200 |
| gagggaggcc | tgggctacag | ccagctgggt | gacgacgacc | tgaaggagac | gggcttccac | 1260 |
| cttaccacca | cgaaccaggg | ggcctctgcc | gcgggccccg | gcttcagcct | caagttctga | 1320 |

<210> SEQ ID NO 27
<211> LENGTH: 2637
<212> TYPE: DNA
<213> ORGANISM: Homo sapiens
<220> FEATURE:
<223> OTHER INFORMATION: PKD2

<400> SEQUENCE: 27

| | | | | | |
|---|---|---|---|---|---|
| atggccaccg | cccctctta | tcccgccggg | ctccctggct | ctcccgggcc | ggggtctcct | 60 |
| ccgccccccg | gcggcctaga | gctgcagtcg | ccgccaccgc | tactgcccca | gatcccggcc | 120 |
| ccgggttccg | gggtctcctt | tcacatccag | atcgggctga | cccgcgagtt | cgtgctgttg | 180 |
| cccgccgcct | ccgagctggc | tcatgtgaag | cagctggcct | gttccatcgt | ggaccagaag | 240 |
| ttccctgagt | gtggcttcta | cggcctttac | gacaagatcc | tgcttttcaa | acatgacccc | 300 |
| acgtcggcca | acctcctgca | gctggtgcgc | tcgtccggag | acatccagga | gggcgacctg | 360 |
| gtggaggtgg | tgctgtcggc | ctcggccacc | ttcgaggact | ccagatccg | cccgcacgcc | 420 |
| ctcacggtgc | actcctatcg | ggcgcctgcc | ttctgtgatc | actgcgggga | gatgctcttc | 480 |
| ggcctagtgc | gccagggcct | caagtgcgat | ggctgcgggc | tgaactacca | caagcgctgt | 540 |
| gccttcagca | tccccaacaa | ctgtagtggg | gcccgcaaac | ggcgcctgtc | atccacgtct | 600 |

```
ctggccagtg gccactcggt gcgcctcggc acctccgagt ccctgccctg cacggctgaa      660
gagctgagcc gtagcaccac cgaactcctg cctcgccgtc ccccgtcatc ctcttcctcc      720
tcttctgcct catcgtatac gggccgcccc attgagctgg acaagatgct gctctccaag      780
gtcaaggtgc cgcacacctt cctcatccac agctatacac ggcccaccgt ttgccaggct      840
tgcaagaaac tcctcaaggg cctcttccgg cagggcctgc aatgcaaaga ctgcaagttt      900
aactgtcaca aaccgctgcg cacccgcgtc cctaatgact gcctggggga ggcccttatc      960
aatggagatg tgccgatgga ggaggccacc gatttcagcg aggctgacaa gagcgccctc     1020
atggatgagt caggagactc cggtgtcatc cctggctccc actcagagaa tgcgctccac     1080
gccagtgagg aggaggaagg cgagggaggc aaggcccaga gctccctggg gtacatcccc     1140
ctaatgaggt tggtgcaatc ggtgcgcaca acgacgcgga atccagcac cacgctgcgg     1200 gagggttggg tggttcatta cagcaacaag gacacgctga aaagcggca ctattggcgc     1260 ctggactgca gtgtatcac gctcttccag aacaacacga ccaacagata ctataaggaa     1320
attccgctgt cagaaatcct cacggtggag tccgcccaga acttcagcct tgtgccgccg     1380
ggcaccaacc cacactgctt tgagatcgtc actgccaatg ccacctactt cgtgggcgag     1440
atgcctggcg ggactccggg tgggccaagt gggcagggg ctgaggccgc ccggggctgg     1500
gagacagcca tccgccaggc cctgatgccc gtcatccttc aggacgcacc cagcgcccca     1560
ggccacgcgc cccacagaca agcttctctg agcatctctg tgtccaacag tcagatccaa     1620
gagaatgtgg acattgccac tgtctaccag atcttccctg acgaagtgct gggctcaggg     1680
cagtttggag tggtctatgg agggaaacac cggaagacag gccgggacgt ggcagttaag     1740
gtcattgaca aactgcgctt ccctaccaag caggagagcc agctccggaa tgaagtggcc     1800
attctgcaga gcctgcggca tcccgggatc gtgaacctgg agtgcatgtt cgagacgcct     1860
gagaaagtgt ttgtggtgat ggagaagctg catggggaca tgttggagat gatcctgtcc     1920
agtgagaagg gccggctgcc tgagcgcctc accaagttcc tcatcaccca gatcctggtg     1980
gctttgagac accttcactt caagaacatt gtccactgtg acttgaaacc agaaaacgtg     2040
ttgctggcat cagcagaccc atttcctcag gtgaagctgt gtgactttgg ctttgctcgc     2100
atcatcggcg agaagtcgtt ccgccgctca gtggtgggca cgccggccta cctggcaccc     2160
gaggtgctgc tcaaccaggg ctacaaccgc tcgctggaca tgtggtcagt gggcgtgatc     2220
atgtacgtca gcctcagcgg caccttccct ttcaacgagg atgaggacat caatgaccag     2280
atccagaacg ccgccttcat gtaccgcgcc agccctgga gccacatctc agctggagcc     2340
attgacctca tcaacaacct gctgcaggtg aagatgcgca aacgctacag cgtggacaaa     2400
tctctcagcc accctggtt acaggagtac cagacgtggc tggacctccg agagctggag     2460
gggaagatgg agagcgata catcacgcat gagagtgacg acgcgcgctg ggagcagttt     2520
gcagcagagc atccgctgcc tgggtctggg ctgccacgg acaggatct cggtggggcc     2580 tgtccaccac aggaccacga catgcagggg ctggcggagc gcatcagtgt tctctga       2637
```

<210> SEQ ID NO 28
<211> LENGTH: 2673
<212> TYPE: DNA
<213> ORGANISM: Homo sapiens
<220> FEATURE:
<223> OTHER INFORMATION: PKD3

<400> SEQUENCE: 28

```
atgtctgcaa ataattcccc tccatcagcc cagaagtctg tattacccac agctattcct       60
```

```
gctgtgcttc cagctgcttc tccgtgttca agtcctaaga cgggactctc tgcccgactc    120
tctaatggaa gcttcagtgc accatcactc accaactcca gaggctcagt gcatacagtt    180
tcatttctac tgcaaattgg cctcacacgg gagagtgtta ccattgaagc ccaggaactg    240
tctttatctg ctgtcaagga tcttgtgtgc tccatagttt atcaaaagtt tccagagtgt    300
ggattctttg gcatgtatga caaaattctt ctctttcgcc atgacatgaa ctcagaaaac    360
attttgcagc tgattacctc agcagatgaa atacatgaag gagacctagt ggaagtggtt    420
ctttcagctt tagccacagt agaagacttc cagattcgtc cacatactct ctatgtacat    480
tcttacaaag ctcctacttt ctgtgattac tgtggtgaga tgctgtgggg attggtacgt    540
caaggactga atgtgaagg ctgtggatta aattaccata acgatgtgc cttcaagatt    600 ccaaataact gtagtggagt aagaaagaga cgtctgtcaa atgtatcttt accaggaccc    660
ggcctctcag ttccaagacc cctacagcct gaatatgtag ccttcccag tgaagagtca    720 catgtccacc aggaaccaag taagagaatt ccttcttgga gtggtcgccc aatctggatg    780
gaaaagatgg taatgtgcag agtgaaagtt ccacacacat ttgctgttca ctcttacacc    840
cgtcccacga tatgtcagta ctgcaagcgg ttactgaaag gcctctttcg ccaaggaatg    900
cagtgtaaag attgcaaatt caactgccat aaacgctgtg catcaaaagt accaagagac    960
tgccttggag aggttacttt caatggagaa ccttccagtc tgggaacaga tacagatata   1020
ccaatggata ttgacaataa tgacataaat agtgatagta gtcggggttt ggatgacaca   1080
gaagagccat cacccccaga agataagatg ttcttcttgg atccatctga tctcgatgtg   1140
gaaagagatg aagaagccgt taaaacaatc agtccatcaa caagcaataa tattccgcta   1200
atgagggttg tacaatccat caagcacaca agaggaagaa gcagcacaat ggtgaaggaa   1260
gggtggatgg tccattacac cagcagggat aacctgagaa agaggcatta ttggagactt   1320
gacagcaaat gtctaacatt atttcagaat gaatctggat caaagtatta taggaaaatt   1380
ccactttcag aaattctccg catatcttca ccacgagatt tcacaaacat ttcacaaggc   1440
agcaatccac actgttttga atcattact gatactatgg tatacttcgt tggtgagaac   1500
aatggggaca gctctcataa tcctgttctt gctgccactg agttggact tgatgtagca   1560 cagagctggg aaaaagcaat tcgccaagcc ctcatgcctg ttactcctca agcaagtgtt   1620
tgcacttctc cagggcaagg gaaagatcac aaagatttgt ctacaagtat ctctgtatct   1680
aattgtcaga ttcaggagaa tgtggatatc agtactgttt accagatctt tgcagatgag   1740
gtgcttggtt caggccagtt tggcatcgtt tatggaggaa acatagaaa gactgggagg   1800 gatgtggcta ttaaagtaat tgataagatg agattcccca caaaacaaga aagtcaactc   1860
cgtaatgaag tggctatttt acagaatttg caccatcctg ggattgtaaa cctggaatgt   1920
atgtttgaaa ccccagaacg agtctttgta gtaatggaaa agctgcatgg agatatgttg   1980
gaaatgattc tatccagtga gaaaagtcgg cttccagaac gaattactaa attcatggtc   2040
acacagatac ttgttgcttt gaggaatctg catttaaga atattgtgca ctgtgattta   2100
aagccagaaa atgtgctgct tgcatcagca gagccatttc ctcaggtgaa gctgtgtgac   2160
tttggatttg cacgcatcat tggtgaaaag tcattcagga gatctgtggt aggaactcca   2220
gcatacttag cccctgaagt tctccggagc aaaggttaca accgttccct agatatgtgg   2280
tcagtgggag ttatcatcta tgtgagcctc agtggcacat ttccttttaa tgaggatgaa   2340
gatataaatg accaaatcca aaatgctgca tttatgtacc caccaaatcc atggagagaa   2400
```

-continued

| | |
|---|---|
| atttctggtg aagcaattga tctgataaac aatctgcttc aagtgaagat gagaaaacgt | 2460 |
| tacagtgttg acaaatctct tagtcatccc tggctacagg actatcagac ttggcttgac | 2520 |
| cttagagaat ttgaaactcg cattggagaa cgttacatta cacatgaaag tgatgatgct | 2580 |
| cgctgggaaa tacatgcata cacacataac cttgtatacc caaagcactt cattatggct | 2640 |
| cctaatccag atgatatgga agaagatcct taa | 2673 |

<210> SEQ ID NO 29
<211> LENGTH: 2955
<212> TYPE: DNA
<213> ORGANISM: Homo sapiens
<220> FEATURE:
<223> OTHER INFORMATION: PKN2

<400> SEQUENCE: 29

| | |
|---|---|
| atggcgtcca acccgaacg gggggagatt ctgctcacgg aactgcaggg ggattcccga | 60 |
| agtcttccgt tttctgagaa tgtgagtgct gttcaaaaat tagacttttc agatacaatg | 120 |
| gtgcagcaga aattggatga tatcaaggat cgaattaaga gagaaataag gaaagaactg | 180 |
| aaaatcaaag aaggagctga aaatctgagg aaagtcacaa cagataaaaa aagtttggct | 240 |
| tatgtagaca acattttgaa aaatcaaat aaaaaattag aagaactaca tcacaagctg | 300 |
| caggaattaa atgcacatat tgttgtatca gatccagaag atattacaga ttgcccaagg | 360 |
| actccagata ctccaaataa tgaccctcgt tgttctacta gcaacaatag attgaaggcc | 420 |
| ttacaaaaac aattggatat agaacttaaa gtaaaacaag gtgcagagaa tatgatacag | 480 |
| atgtattcaa atggatcttc aaaggatcgg aaactccatg gtacagctca gcaactgctc | 540 |
| caggacagca agacaaaaat agaagtcata cgatgcagaa ttcttcaggc agtccagact | 600 |
| aatgaattgg cttttgataa tgcaaaacct gtgataagtc ctcttgaact tcggatggaa | 660 |
| gaattaaggc atcattttag atagagtttt gcagtagcag aaggtgcaaa gaatgtaatg | 720 |
| aaattacttg gctcaggaaa agtaacagac agaaaagcac tttcagaagc tcaagcaaga | 780 |
| tttaatgaat caagtcagaa gttggacctt ttaaagtatt cattagagca agattaaac | 840 |
| gaagtcccca gaatcatcc caaaagcagg attattattg aagaacttc acttgttgct | 900 |
| gcatcaccaa cactaagtcc acgtcaaagt atgatatcta cgcaaaatca atatagtaca | 960 |
| ctatccaaac cagcagcact aacaggtact ttggaagttc gtcttatggg ctgccaagat | 1020 |
| atcctagaga atgtccctgg acggtcaaaa gcaacatcag ttgcactgcc tggttggagt | 1080 |
| ccaagtgaaa ccagatcatc tttcatgagc agaacgagta aaagtaaaag cggaagtagt | 1140 |
| cgaaatcttc taaaaaccga tgacttgtcc aatgatgtct gtgctgtttt gaagctcgat | 1200 |
| aatactgtgg ttggccaaac tagctggaaa cccatttcca atcagtcatg ggaccagaag | 1260 |
| tttacactgg aactggacag gtcacgtgaa ctggaaattt cagtttattg gcgtgattgg | 1320 |
| cggtctctgt gtgctgtaaa atttctgagg ttagaagatt ttttagacaa ccaacggcat | 1380 |
| ggcatgtgtc tctatttgga accacagggt actttatttg cagaggttac ctttttaat | 1440 |
| ccagttattg aaagaagacc aaaacttcaa agacaaaaga aaattttttc aaagcaacaa | 1500 |
| ggcaaaacat ttctcagagc tcctcaaatg aatattaata ttgccacttg gggaaggcta | 1560 |
| gtaagaagag ctattcctac agtaaatcat tctggcacct tcagcccatca agctcctgtg | 1620 |
| cctactacag tgccagtggt tgatgtacgc atccctcaac tagcacctcc agctagtgat | 1680 |
| tctacagtaa ccaaattgga cttcgatctt gagcctgaac ctcctccagc cccaccacga | 1740 |
| gcttcttctc ttggagaaat agatgaatct tctgaattaa gagttttgga tataccagga | 1800 |

| | |
|---|---|
| caggattcag agactgtttt tgatattcag aatgacagaa atagtatact tccaaaatct | 1860 |
| caatctgaat acaagcctga tactcctcag tcaggcctag aatatagtgg tattcaagaa | 1920 |
| cttgaggaca gaagatctca gcaaaggttt cagtttaatc tacaagattt caggtgttgt | 1980 |
| gctgtcttgg gaagaggaca ttttggaaag gtgcttttag ctgaatataa aaacacaaat | 2040 |
| gagatgtttg ctataaaagc cttaaagaaa ggagatattg tggctcgaga tgaagtagac | 2100 |
| agcctgatgt gtgaaaaaag aatttttgaa actgtgaata gtgtaaggca tccctttttg | 2160 |
| gtgaaccttt ttgcatgttt ccaaaccaaa gagcatgttt gctttgtaat ggaatatgct | 2220 |
| gccggtgggg acctaatgat gcacattcat actgatgtct tttctgaacc aagagctgta | 2280 |
| ttttatgctg cttgtgtagt tcttgggttg cagtatttac atgaacacaa aattgtttat | 2340 |
| agagatttga aattggataa cttattgcta gatacagagg gctttgtgaa aattgctgat | 2400 |
| tttggtcttt gcaaagaagg aatgggatat ggagatagaa caagcacatt ttgtggcact | 2460 |
| cctgaatttc ttgccccaga agtattaaca gaaacttctt atacaagggc tgtagattgg | 2520 |
| tggggccttg gcgtgcttat atatgaaatg cttgttggtg agtctcccct tcctggtgat | 2580 |
| gatgaagagg aagttttga cagtattgta aatgatgaag taaggtatcc aaggttctta | 2640 |
| tctacagaag ccatttctat aatgagaagg ctgttaagaa gaaatcctga acggcgcctt | 2700 |
| ggggctagcg agaaagatgc agaggatgta aaaaagcacc cattttttccg gctaattgat | 2760 |
| tggagcgctc tgatggacaa aaaagtaaag ccaccattta tacctaccat aagaggacga | 2820 |
| gaagatgtta gtaattttga tgatgaattt acctcagaag cacctattct gactccacct | 2880 |
| cgagaaccaa ggatacttc ggaagaggag caggaaatgt tcagagattt tgactacatt | 2940 |
| gctgattggt gttaa | 2955 |

<210> SEQ ID NO 30
<211> LENGTH: 1308
<212> TYPE: DNA
<213> ORGANISM: Homo sapiens
<220> FEATURE:
<223> OTHER INFORMATION: SgK495

<400> SEQUENCE: 30

| | |
|---|---|
| atgaagcgga gagcatcaga cagaggagct ggggaaacgt cggccagggc caaggctcta | 60 |
| ggaagtggga tttctggaaa taatgcaaag agagctggac cattcatcct tggtccccgt | 120 |
| ctgggcaact caccggtgcc aagcatagtg cagtgtttgg cgaggaaaga tggcacggat | 180 |
| gacttctatc agctgaagat cctgaccctg gaggagaggg gggaccaagg catagagagc | 240 |
| caggaagagc ggcagggcaa gatgctgctg cacaccgagt actcactgct gtctctcctg | 300 |
| cacacgcagg atggcgtggt gcaccaccac ggcctcttcc aggaccgcac ctgtgaaatc | 360 |
| gttgaggaca cagaatccag ccggatggtt aagaagatga gaagcgcat ctgcctcgtc | 420 |
| ctggactgcc tctgtgctca tgacttcagc gataagaccg ctgacctcat caacctgcag | 480 |
| cactacgtca tcaaggagaa gaggctcagc gagagggaga ctgtggtaat cttctacgac | 540 |
| gtggtccgcg tggtggaggc cctgcaccag aaaaatatcg tgcacagaga cctgaagctg | 600 |
| gggaacatgg tgctcaacaa gagacacat cggataacca tcaccaactt ctgcctcggg | 660 |
| aagcatctgg tgagcgaggg ggacctgctg aaggaccaga gagggagccc tgcctacatc | 720 |
| agtcccgacg tgctcagcgg ccggccgtac gtggcaagc ccagtgacat gtgggccctg | 780 |
| ggcgtggtgc tcttcaccat gctgtatggc cagttcccct tctacgacag catcccgcag | 840 |

```
gagctcttcc gcaagatcaa ggctgccgag tataccattc ctgaggatgg acgggtttct      900
gagaacaccg tgtgtctcat ccggaagctg ctggtccttg accccagca gcgcctggcc      960 gccgccgacg tcctggaggc cctcagtgcc atcattgcat catggcagtc cctgtcatct    1020
ctgagtgggc ctttgcaagt ggttcctgac attgatgacc aaatgagcaa tgcggatagc    1080
tcccaggagg cgaaggtgac ggaggagtgc tcccagtacg agtttgagaa ctacatgcgt    1140
cagcagctgc tgctggccga ggagaagagc tccatccatg acgcccggag ctgggtaccc    1200
aagcggcagt tcggcagcgc accaccggtg cgacggctgg ccacgacgc acagcccatg     1260 acctccttgg acacggccat cctggcgcag cgctacctgc ggaaataa                 1308

<210> SEQ ID NO 31
<211> LENGTH: 564
<212> TYPE: DNA
<213> ORGANISM: Homo sapiens
<220> FEATURE:
<223> OTHER INFORMATION: skMLCK

<400> SEQUENCE: 31
atgaacatcc tgtgtgtcaa caccaccggg catttggtga agatcattga ctttggcctg      60
gcacggaggt ataaccccaa cgagaagctg aaggtgaact ttgggacccc agagttcctg     120
tcacctgagg tggtgaatta tgaccaaatc tccgataaga cagacatgtg gagtatgggg    180
gtgatcacct acatgctgct gagcggcctc tccccttcc tgggagatga tgacacagag     240
accctaaaca cgttctatc tggcaactgg tactttgatg aagagacctt tgaggccgta     300
tcagacgagg ccaaagactt tgtctccaac ctcatcgtca aggaccagag ggcccggatg    360
aacgctgccc agtgtctcgc ccatccctgg ctcaacaacc tggcggagaa agccaaacgc    420
tgtaaccgac gccttaagtc ccagatcttg cttaagaaat acctcatgaa gaggcgctgg    480
aagaaaaact tcattgctgt cagcgctgcc aaccgcttca gaagatcag cagctcgggg    540 gcactgatgg ctctgggggt ctga                                            564

<210> SEQ ID NO 32
<211> LENGTH: 1968
<212> TYPE: DNA
<213> ORGANISM: Homo sapiens
<220> FEATURE:
<223> OTHER INFORMATION: SRPK1

<400> SEQUENCE: 32
atggagcgga aagtgcttgc gctccaggcc cgaaagaaaa ggaccaaggc caagaaggac       60
aaagcccaaa ggaaatctga aactcagcac cgaggctctg ctccccactc tgagagtgat     120
ctaccagagc aggaagagga gattctggga tctgatgatg atgagcaaga agatcctaat     180
gattattgta aggaggttta tcatcttgtg aaaattggag atctattcaa tgggagatac    240
catgtgatcc gaaagttagg ctggggacac ttttcaacag tatggttatc atgggatatt    300 cagggggaaga aatttgtggc aatgaaagta gttaaaagtg ctgaacatta cactgaaaca    360
gcactagatg aaatccggtt gctgaagtca gttcgcaatt cagaccctaa tgatccaaat    420
agagaaatgg ttgttcaact actagatgac tttaaaatat caggagttaa tggaacacat    480
atctgcatgg tatttgaagt tttggggcat catctgctca gtggatcat caaatccaat    540 tatcagggc ttccactgcc ttgtgtcaaa aaaattattc agcaagtgtt acagggtctt    600
gattatttac ataccaagtg ccgtatcatc cacactgaca ttaaaccaga gaacatctta    660
ttgtcagtga atgagcagta cattcggagg ctggctgcag aagcaacaga atggcagcga    720
```

-continued

```
tctggagctc ctccgccttc cggatctgca gtcagtactg ctccccagcc taaaccagct    780
gacaaaatgt caaagaataa gaagaagaaa ttgaagaaga agcagaagcg ccaggcagaa    840
ttactagaga agcgaatgca ggaaattgag gaaatggaga agagtcggg ccctgggcaa     900 aaaagaccaa acaagcaaga agaatcagag agtcctgttg aaagacccct gaaagagaac    960
ccacctaata aaatgaccca agaaaaactt gaagagtcaa gtaccattgg ccaggatcaa   1020
acgcttatgg aacgtgatac agagggtggt gcagcagaaa ttaattgcaa tggagtgatt   1080
gaagtcatta attatactca gaacagtaat aatgaaacat tgagacataa agaggatcta   1140
cataatgcta atgactgtga tgtccaaaat ttgaatcagg aatctagttt cctaagtctc   1200
ccaaatggag acagcagcac atctcaagaa acagactctt gtacacctat aacatctgag   1260
gtgtcagaca ccatggtgtg ccagtcttcc tcaactgtag gtcagtcatt cagtgaacaa   1320
cacattagcc aacttcaaga aagcattcgg gcagagatac cctgtgaaga tgaacaagag   1380
caagaacata acggaccact ggacaacaaa ggaaaatcca cggctggaaa ttttcttgtt   1440
aatccccttg agccaaaaaa tgcagaaaag ctcaaggtga agattgctga ccttggaaat   1500
gcttgttggg tgcacaaaca tttcactgaa gatattcaaa caaggcaata tcgttccttg   1560
gaagttctaa tcggatctgg ctataatacc cctgctgaca tttggagcac ggcatgcatg   1620
gcctttgaac tggccacagg tgactatttg tttgaacctc attcagggga agagtacact   1680
cgagatgaag atcacattgc attgatcata gaacttctgg ggaaggtgcc tcgcaagctc   1740
attgtggcag gaaaatattc caaggaattt ttcaccaaaa aaggtgacct gaaacatatc   1800
acgaagctga aaccttgggg cctttttgag gttctagtgg agaagtatga gtggtctcag   1860
gaagaggcag ctggcttcac agatttctta ctgcccatgt tggagctgat ccctgagaag   1920
agagccactg ccgccgagtg tctccggcac ccttggctta actcctaa                1968
```

<210> SEQ ID NO 33
<211> LENGTH: 2001
<212> TYPE: DNA
<213> ORGANISM: Homo sapiens
<220> FEATURE:
<223> OTHER INFORMATION: TNK1

<400> SEQUENCE: 33

```
atgcttcccg aggctggctc cctgtggcta ctgaagctgc tccgggacat ccagttggcc     60 cagtttttact ggcccatcct agaggagctt aatgtcaccc ggccagggca cttcgacttt    120
gtaaagcctg aggacctgga cggcattggc atgggccggc ctgcccaacg cagactgtcc    180
gaagctctga aaagcctacg ttctgggcct aagtctaaga actgggtcta caagatcctt    240
ggaggttttg ccctgagca aaggagccc accctgccca ggacagccc acggcacctc       300 cctgagccag aggggggcct caagtgtctg atcccagagg gtgctgtttg cagaggggag    360 ctgctggtt caggctgctt cggtgtggtg caccgagggc tgtggacgct gcccagtggc    420
aagagtgtcc cagtggctgt caagtccctc cgggtaggtc ccgaaggccc gatgggcaca    480
gaactggggg acttcctgcg agaggtatcg gtcatgatga acttggagca cccacacgtg    540
ctgcgtctgc acggccttgt actgggccag cctctgcaga tggtgatgga gctggcgcca    600
ctgggctccc tgcacgcgcg cttaacggcc ccggccccga caccccgct gctcgtggcc    660 ctgctctgcc tcttcctgcg gcagctggcg ggagccatgg cgtacctggg ggccgcgggg    720
ctggtgcacc gagacctcgc tacgcgcaac ctacagctgg cgtcgccgcg caccatcaag    780
```

-continued

```
gtggctgact tcgggctggt gcggcctctg ggcggtgccc ggggccgcta cgtcatgggc      840
gggccccgcc ctatccccta cacctggtgt gccccagaga gcctgcgcca cggagccttc      900
tcgtctgcct cggacgtgtg gatgtttggg gtgacgctgt gggagatgtt ctccgggggc      960
gaggaaccct ggcccggggt cccaccgtac ctcatcctgc agcggctgga ggacagagcc     1020
cggctgccta ggcctccccc ctcctccagg gccctctact ccctcgcctt gcgctgctgg     1080 gcccccacc ctgccgaccg gcctagcttt tcccacctgg aggggctgct gcaagaggcc     1140
gggccttcgg aagcatgttg tgtgagggat gccacagaac caggcgccct gaggatggag     1200
actggtgacc ccatcacagt catcgagggc agctcctctt tccacagccc cgactccaca     1260
atctggaagg accagaatgg tcgcaccttc aaagtgggca gcttcccagc ctcggcagtg     1320
acgctgacag atgcgggggg cttgccagcc acccgtccag tccacagagg cacccctgcc     1380
cggggagatc aacacccagg aagcatagat ggagacagaa agaaggcaaa tctttgggat     1440 gcgccccag cacggggcca gaggaggaac atgcccctgg agaggatgaa aggcatttcc     1500
aggagtctgg agtcagttct gtccctcggt cctcgtccca caggggtgg ttcaagcccc     1560 cctgaaattc gacaagccag agctgtgccc cagggacctc caggcctgcc tccacgccca     1620
cctttatcct ctagctctcc tcagcccagc cagccctcta gggagaggct ccctggccc     1680 gaaagaaaac ccccacacaa tcaccccatg ggaatgcctg gagcccgtaa agccgctgcc     1740
ctctctggag gcctcttgtc cgatcctgag ttgcagagga agattatgga aatggagctg     1800
agtgtgcatt gggtcaccca ccaggagtgc cagacagcac taggagccac tgggggagat     1860
gtggcttctg ccatccggaa cctcaaggta gatcagctct tcctcctgag tagccggtcc     1920
agagctgact gctggcgcat cctggagcat taccagtggg acctctcagc tgccagccgt     1980
tatgtcctgg ccaggccctg a                                                2001
```

<210> SEQ ID NO 34
<211> LENGTH: 1032
<212> TYPE: DNA
<213> ORGANISM: Homo sapiens
<220> FEATURE:
<223> OTHER INFORMATION: Trb2

<400> SEQUENCE: 34

```
atgaacatac acaggtctac ccccatcaca atagcgagat atgggagatc gcggaacaaa       60
acccaggatt tcgaagagtt gtcgtctata aggtccgcgg agcccagcca gagtttcagc      120
ccgaacctcg gctccccgag cccgcccgag actccgaact tgtcgcattg cgtttcttgt      180
atcgggaaat acttattgtt ggaacctctg gagggagacc acgttttccg tgccgtgcat      240
ctgcacagcg gagaggagct ggtgtgcaag gtgtttgata tcagctgcta ccaggaatcc      300
ctggcaccgt gcttttgcct gtctgctcat agtaacatca accaaatcac tgaaattatc      360
ctgggtgaga ccaaagccta tgtgttcttt gagcgaagct atgggacat gcattccttc      420 gtccgcacct gcaagaagct gagagaggag gaggcagcca gactgttcta ccagattgcc      480
tcggcagtgg cccactgcca tgacgggggg ctggtgctgc ggacctcaa gctgcgaaa      540 ttcatcttta aggacgaaga gaggactcgg gtcaagctgg aaagcctgga agacgcctac      600
attctgcggg gagatgatga ttccctctcc gacaagcatg gctgcccggc ttacgtaagc      660
ccagagatct gaacaccag tggcagctac tcgggcaaag cagccgacgt gtggagcctg      720 gggtgatgc tgtacaccat gttggtgggg cggtaccctt tccatgacat tgaacccagc      780 tcccctcttca gcaagatccg gcgtggccag ttcaacattc agagactctg tcgcccaag      840
```

```
gccaagtgcc tcatccgaag cattctgcgt cgggagccct cagagcggct gacctcgcag    900
gaaattctgg accatccttg gttttctaca gattttagcg tctcgaattc agcatatggt    960
gctaaggaag tgtctgacca gctggtgccg gacgtcaaca tggaagagaa cttggaccct   1020
ttctttaact ga                                                       1032
```

```
<210> SEQ ID NO 35
<211> LENGTH: 1077
<212> TYPE: DNA
<213> ORGANISM: Homo sapiens
<220> FEATURE:
<223> OTHER INFORMATION: Trb3

<400> SEQUENCE: 35
atgcgagcca cccctctggc tgctcctgcg ggttccctgt ccaggaagaa gcggttggag     60
ttggatgaca acttagatac cgagcgtccc gtccagaaac gagctcgaag tgggccccag    120
cccagactgc cccctgcct gttgcccctg agcccaccta ctgctccaga tcgtgcaact    180
gctgtggcca ctgcctcccg tcttgggccc tatgtcctcc tggagcccga ggagggcggg    240
cgggcctacc aggccctgca ctgccctaca ggcactgagt atacctgcaa ggtgtacccc    300
gtccaggaag ccctggccgt gctggagccc tatgcgcggc tgccccgca caagcatgtg    360 gctcggccca ctgaggtcct ggctggtacc cagctcctct acgccttttt cactcggacc    420 catgggggaca tgcacagcct ggtgcgaagc cgccaccgta tccctgagcc tgaggctgcc    480
gtgctcttcc gccagatggc caccgccctg gcgcactgtc accagcacgg tctggtcctg    540
cgtgatctca agctgtgtcg ctttgtcttc gctgaccgtg agaggaagaa gctggtgctg    600
gagaacctgg aggactcctg cgtgctgact gggccagatg attccctgtg ggacaagcac    660
gcgtgcccag cctacgtggg acctgagata ctcagctcac gggcctcata ctcgggcaag    720
gcagccgatg tctggagcct gggcgtggcg ctcttcacca tgctggccgg ccactacccc    780
ttccaggact cggagcctgt cctgctcttc ggcaagatcc gccgcgggggc ctacgccttg    840 cctgcaggcc tctcggcccc tgcccgctgt ctggttcgct gcctccttcg tcgggagcca    900
gctgaacggc tcacagccac aggcatcctc ctgcacccct ggctgcgaca ggacccgatg    960
cccttagccc caacccgatc ccatctctgg gaggctgccc aggtggtccc tgatggactg   1020
gggctggacg aagccaggga agaggaggga gacagagaag tggttctgta ggctag        1077
```

```
<210> SEQ ID NO 36
<211> LENGTH: 1077
<212> TYPE: DNA
<213> ORGANISM: Homo sapiens
<220> FEATURE:
<223> OTHER INFORMATION: TSSK2

<400> SEQUENCE: 36
atggacgatg ccacagtcct aaggaagaag ggttacatcg taggcatcaa tcttggcaag     60
ggttcctacg caaagtcaa atctgcctac tctgagcgcc tcaagttcaa tgtggctgtc    120
aagatcatcg accgcaagaa acacctact gactttgtgg agagattcct tcctcgggag    180
atggacatcc tggcaactgt caaccacggc tccatcatca agacttacga gatctttgag    240
acctctgacg gacggatcta catcatcatg gagcttggcg tccagggcga cctcctcgag    300
ttcatcaagt gccagggagc cctgcatgag acgtggcac gcaagatgtt ccgacagctc    360
tcctccgccg tcaagtactg ccacgacctg gacatcgtcc accggaccct caagtgcgag    420
```

```
aaccttctcc tcgacaagga cttcaacatc aagctgtctg actttggctt ctccaagcgc      480
tgcctgcggg acagcaatgg gcgcatcatc ctcagcaaga ccttctgcgg gtcggcagca      540
tatgcagccc ccgaggtgct gcagagcatc ccctaccagc ccaaggtgta tgacatctgg      600
agcctgggcg tgatcctgta catcatggtc tgcggctcca tgccctatga cgactccgac      660
atcaggaaga tgctgcgtat ccagaaggag caccgtgtgg acttcccgcg ctccaagaac      720
ctgacctgcg agtgcaagga cctcatctac cgcatgctgc agcccgacgt cagccagcgg      780
ctccacatcg atgagatcct cagccactcg tggctgcagc cccccaagcc caaagccacg      840
tcttctgcct ccttcaagag ggaggggag ggcaagtacc gcgctgagtg caaactggac       900
accaagacag gcttgaggcc cgaccaccgg cccgaccaca agcttggagc caaaacccag      960
caccggctgc tggtggtgcc cgagaacgag aacaggatgg aggacaggct ggccgagacc     1020
tccagggcca aagaccatca catctccgga gctgaggtgg ggaaagcaag cacctag        1077
```